(12) United States Patent
Mecozzi et al.

(10) Patent No.: US 8,900,562 B2
(45) Date of Patent: Dec. 2, 2014

(54) SEMI-FLUORINATED BLOCK COPOLYMERS FOR DELIVERY OF THERAPEUTIC AGENTS

(75) Inventors: Sandro Mecozzi, Madison, WI (US); Glen S. Kwon, Waunakee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1617 days.

(21) Appl. No.: 11/972,061

(22) Filed: Jan. 10, 2008

(65) Prior Publication Data

US 2008/0194500 A1 Aug. 14, 2008

Related U.S. Application Data

(60) Provisional application No. 60/884,672, filed on Jan. 12, 2007.

(51) Int. Cl.

| | | |
|---|---|---|
| *A61K 31/74* | (2006.01) | |
| *A61K 9/107* | (2006.01) | |
| *A61K 8/90* | (2006.01) | |
| *A61K 31/335* | (2006.01) | |
| *A61K 31/337* | (2006.01) | |
| *A61K 31/395* | (2006.01) | |
| *A61K 31/4353* | (2006.01) | |
| *A61K 31/704* | (2006.01) | |
| *C08L 51/00* | (2006.01) | |
| *C08L 53/00* | (2006.01) | |

(52) U.S. Cl.
CPC .................. *A61K 9/1075* (2013.01); *A61K 8/90* (2013.01); *A61K 31/335* (2013.01); *A61K 31/337* (2013.01); *A61K 31/395* (2013.01); *A61K 31/4353* (2013.01); *A61K 31/704* (2013.01); *C08L 51/003* (2013.01); *C08L 53/00* (2013.01)
USPC .................... 424/78.17; 424/78.08; 424/78.37

(58) Field of Classification Search
CPC ............................. A61K 8/90; A61K 9/1075
USPC .................. 424/78.08, 78.17, 78.37
See application file for complete search history.

(56) References Cited

U.S. PATENT DOCUMENTS

| | | | |
|---|---|---|---|
| 5,733,526 | A | 3/1998 | Trevino et al. |
| 5,914,352 | A | 6/1999 | Weers et al. |
| 5,929,177 | A | 7/1999 | Kataoka et al. |
| 6,113,919 | A | 9/2000 | Reiss et al. |
| 6,316,505 | B1 | 11/2001 | Kabanov et al. |
| 6,322,805 | B1 | 11/2001 | Kim et al. |
| 6,444,660 | B1 | 9/2002 | Unger et al. |
| 6,808,720 | B2 | 10/2004 | Unger et al. |
| 6,903,173 | B2 | 6/2005 | Cernohous et al. |
| 7,018,655 | B2 | 3/2006 | Lele et al. |
| 2004/0116360 | A1* | 6/2004 | Kwon ............ 514/28 |
| 2005/0033132 | A1 | 2/2005 | Shults et al. |
| 2005/0214379 | A1 | 9/2005 | Mecozzi et al. |
| 2005/0220880 | A1 | 10/2005 | Lewis et al. |
| 2005/0287196 | A1 | 12/2005 | Cho et al. |
| 2006/0240092 | A1 | 10/2006 | Breitenkamp et al. |
| 2008/0234389 | A1 | 9/2008 | Mecozzi et al. |

FOREIGN PATENT DOCUMENTS

| | | |
|---|---|---|
| RU | 2162692 | 2/2001 |
| WO | WO 2005/067517 | 7/2005 |
| WO | WO 2008/070490 | 6/2008 |

OTHER PUBLICATIONS http://www.merriamwebster.com /dictionary/derivative.*
Stella et al. Expert Opinion of Therapeutic Patents, 2004 14(3): 277-280).*
Ettmeyer, peter et al. J. Med. Chem. 2004 47(10) 2394.*
Testa, Bernard Biochemical Pharmacology 68 (2004) 2097-2106.*
Wolff M. Burger's Medicinal Chemistry and Drug Discovery Fifth Edition vol. I: Principles abd Practice pp. 975-977.*
Testa, Caldwell Medicinal Research Reviews, 16(3):233-241, ed. John Wiley & Sons (1996).*
Adams et al. (2003) "Relative Aggregation State and Hemolytic Activity of Amphotericin B Encapsulated by Poly(Ethylene Oxide)-*Block*-poly(*N*-hexyl-L-aspartamide)-acyl Conjugate Micelled: Effects of Acyl Chain Length," *J. Control. Release* 87:23-32.
Buszello et al. (2000) Emulsions as Drug Delivery Systems, In; *Pharmaceutical Emulsions and Suspensions*, Nielloud et al. Eds., Marcel Dekker: New York, 105:191-228.
Cuignet et al. (2002) "A Second-Generation Blood Substitute (Perflubron Emulsion) Increases the Blood Solubility of Modern Volatile Anesthetics In Vitro," *Anesth Analg.* 95:368-372.
Definition of the Word "Derivative," http://www.merriamwebster.com/dictionary/derivative , Downloaded Jan. 27, 2011.
Ettmayer et al. (May 6, 2004) "Lessons Learned from Marketed and Investigational Prodrugs," *J. Med. Chem*.47(10):2393-2404.
Fast et al. (Oct. 2008) "Fluoropolymer-Based Emulsions for the Intravenous Delivery of Sevoflurane," *Anesthesiology* 109(4):651-656.

(Continued)

*Primary Examiner* — James Rogers
(74) *Attorney, Agent, or Firm* — Lathrop & Gage LLP

(57) ABSTRACT

The present invention provides semi-fluorinated block copolymers and related methods of synthesizing and using semi-fluorinated block copolymers for drug delivery and drug formulation applications. Semi-fluorinated block copolymers of this aspect of the invention include block copolymers having discrete hydrophilic, fluorophilic and hydrophobic structural domains that are capable of forming supramolecular structures in aqueous solutions, such as micelles, for encapsulating hydrophobic and/or fluorophilic therapeutic agents. Encapsulation by semi-fluorinated block copolymers of the present invention allows for enhanced solubilization and stabilization of hydrophobic and/or fluorophilic therapeutic agents relative to conventional drug delivery compositions and methods.

25 Claims, 4 Drawing Sheets

(56) References Cited

OTHER PUBLICATIONS

Ferstandig, L.L. (1995) "Fluorinated Anesthetics," In; *Chemistry of Organic Fluorine Compounds II: A Critical Review*, Hudlický et al. Eds., ACS Monograph No. 18, American Chemical Society, Washington, D.C., pp. 1133-1137.

Hillaireau et al. (2006) "Polymeric Nanoparticles as Drug Carriers," In; *Polymers in Drug Delivery*, Uchegbu et al. Eds., CRC: Boca Raton, pp. 101-110.

Office Action and Response Corresponding to U.S. Appl. No. 11/946,174 Mailed Jan. 19, 2011 and May 19, 2011.

Office Actions and Response Corresponding to U.S. Appl. No. 11/028,948, Mailed between Aug. 1, 2008 and Apr. 15, 2009.

Riess et al. (1988) "Design, Synthesis and Evaluation of Fluorocarbons and Surfactants for in Vivo Applications New Perfluoroalkylated Polyhydroxylated Surfactants," *Biomat. Art. Cells Art. Org.* 16(1-3):421-430.

Stella, V.J. (2004) "Prodrugs as Therapeutics," *Exp. Opin. Ther. Patents.* 14(3):277-280.

Strickley, R.G. (Feb. 2004) "Solubilizing Excipients in Oral and Injectable Formulations," *Pharm. Res.* 21(2):201-230.

Testa et al. (1996) "Prodrugs Revisited: the 'Ad Hoc' Approach as a Complement to Ligand Design," *Med. Res. Rev.* 16(3):233-241.

Testa, B. (2004) "Prodrugs Research: Futile or Fertile," *Biochemical Pharmacology* 68:2097-2106.

Torchilin, V.P. (2004) "Targeted Polymeric Micelled for Delivery of Poorly Soluble Drugs," *CLMS Cell. Mol. Life Sci.* 61:2549-2559.

van den Temple, M. (1953) "Stability of Oil-In-Water Emulsions II; Mechanism of the Coagulation of an Emulsion," *Recl. Trav. Chim. Pays-Bas* 72:433-441.

Walstra et al. (1998) "Emulsion Formation," In; *Modern Aspects of Emulsion Science*, Binks, B. Ed., The Royal Society of Chemistry: Cambridge, pp. 56-99.

Wang et al. (2007) "Formulation, Preparation and Evaluation of Flunarizine-Loaded Lipid Microspheres," *J. Pharm. Pharmacol.* 59:351-357.

Weers et al. (1994) "Room Temperature Stable Perfluorocarbon Emulsions with Acceptable Half-Lives in the Reticuloendotherlial System," *Art. Cells Blood Subs. Immob. Biotech.* 22(4):1175-1182.

Wolff, M.E. (1994) Burger's Medicinal Chemistry and Drug Discovery vol. 1., *Principles and Practice*, 5th Ed. pp: 975-977.

Written Opinion Corresponding to International Application No. PCT/US05/00100, Mailed Jul. 12, 2006.

Yu et al. (2006) "Formulation and Evaluation of Nimodipine-Loaded Lipid Microspheres," *J. Pharm. Pharmacol.* 8:1429-1435.

Jee et al. (Jul. 8, 2011) "Encapsulation and Release of Amphotericin B from an ABC Triblock Fluorous Copolymer," *Pharm Res.* (Jan. 2012) 29(1):69-82.

Abrol et al. (2004) "Formulation, Characterization and In Vitro Evaluation of Silymarin-Loaded Microspheres," *Drug Deliv.* 11:185-191.

Adams et al. (2003) "Amphiphilic Block Copolymers for Drug Delivery," *J. Pharm. Sci.* 92:1343-1355.

Akkar et al. (2003) "Formulation of Intravenous Carbamzepine Emulsions by SolEmuls Technology," *Eur. J. Pharmaceutics Biopharmaceutics* 55:305-312.

Akkar et al. (2003) "Intravenous Itraconazole Emulsion Produced by SolEmuls Technology," *Eur. J. Pharaceutics Biopharmaceutics* 56:29-36.

Akkar et al. (2004) "Solubilizing Poorly Soluble Antimycotic Agents by Emulsification Via a Solvent-Free Process," *AAPS PharmSciTech* 5(1).

Ashok et al. (2004) "In Vitro Characterization of PEGylated Phospholipid Micelles for Improved Drug Solubilization: Effects of PEG Chain Length and PC Incorporation," *J. Pharm. Sci.* 93(10):2476-2487.

Benita et al. (1993) "Submicron Emulsions as Colloidal Drug Carriers for Intravenous Administration: Comprehensive Physiocochemical Characterization," *J. Pharmaceutical Sci.* 82(11):1069-1079.

Benkwitz et al. (2004) "Influence of $GABA_A$ Receptor $\gamma 2$ Splice Variants on Receptor Kinetics and Isoflurane Modulation," *Anesthesiology* 101:924-936.

Biber et al. (1984) "Intravenous Infusion of Halothane Dissolved in Fat. Haemodynamic Effects in Dogs," *Acta Anaesthesiol Scand.* 28:385-389.

Bilgicer et al. (2001) "Programmed Self-Sorting of Coiled Coils with Leucine and Hexafluoroleucine Cores," *J. Am. Chem. Soc.* 123:11815-11816.

Bilgicer et al. (2002) "Synthesis and Thermodynamic Characterization of Self-Sorting Coiled Coils," *Tetrahedron* 58:4105-4112.

Boileau et al. (1999) "Identification of Transduction Elements for Benzodiazepine Modulation of the GABA(A) Receptor: Three Residues are Required for Allosteric Coupling," *J. Neurosci.* 19:10213-10220.

Boileau et al. (2003) "Effects of $\gamma 2S$ Subunit Incorporation on $GABA_A$ Receptor Macroscopic Kinetics," *Neuropharmacology* 44:1003-1012.

Bourdon et al. (2000) "A Comparative Study of the Cellular Uptake, Localization and Photoxicity of *meta*-tetra (hydroxyphenyl) Chlorine Encapsulated in Surface-Modified Submicronic Oil/Water Carriers in HT29 Tumor Cells," *J. Photochem. Photobiol. B Biol.* 55:164-171.

Burt et al. (1999) "Development of Copolymers of Poly(D,L-Lactide) and Methoxypolyethylene Glycols as Micellar Carriers of Paclitaxel," *Coll. Surf. B. Biointerfaces* 16:191-171.

Capek, I. (2004) "Degradation of Kinetically-Stable o/w Emulsions," *Adv. Colloid Interface Sci.* 107:125-155.

Chansri et al. (2006) "Inhibition of Liver Metastasis by all-*trans* retinoic Acid Incorporated into O/W Emulsions in Mice," *Int. J. Pharmaceutics* 321(1-2):42-49.

Chesney et al. (2003) "Differential Uptake of Volatile Agents into Brain Tissue in Vitro. Measurement and Application of a Diffusion Model to Determine Concentration Profiles in Brain Slices," *Anesthesiology* 99:122-130.

Chiari et al. (2004) "Intravenous Emulsified Halogenated Anesthetics Produce Acute and Delayed Preconditioning Against Myocardial Infarction in Rabbits," *Anethesiology* 101:1160-1166.

Constantinides et al. (2000) "Formulation Development and Antitumor Activity of a Filter-Sterilizable Emulsion of Paclitaxel," *Pharmaceutical Research* 17(2):175-182.

Cruz et al. (2006) "Physico-Chemical Characterization and in Vivo Evaluation of Indomethacin Ethyl-Ester-Loaded Nanocapsules by PCS, TEM, SAXS, Interfacial Alkaline Hydrolysis and Antiedematogenic Activity," *J. Nanoscience Nanotechnol.* 6:3154-3162.

Cuignet et al. (2002) "A Second-Generation Blood Substitute (Perflubron Emulsion) Increases the Blood Solubility of Modern Volatile Anesthetics," *Anesth. Analg.* 95:368-372.

Davis et al. (Apr. 1981) "Ostwald Ripening and the Stability of Emulsion Systems: An Explanation for the Effect of an Added Third Component," *J. Colloid Interface Sci.* 80(2):508-511.

De Smet et al. (1999) "Ostwald Ripening of Alkane Emulsions in the presence of Surfactant Micelles," *Langmuir* 15:6745-6754.

Dias et al. (2007) "Pharmacokinetics and Tumor Uptake of a Derivatized Form of Paclitaxel Associated to a Cholesterol-Rich Nanoemulsion (LDE) in Patients in Gynecologic Cancers," *Cancer Chemother. Pharmacol.* 59:105-111.

Dong et al. (1984) "The Py Scale of Solvent Polarities," *Can. J. Chem.* 62:2560-2565.

Driscoll, D.F. (2006) "Lipid Injectable Emulsions: Pharmacopeial and Safety Issues," *Pharmaceutical Res.* 23(9):1959-1969.

Eger, E.I. (1998) "Current and Future Perspectives on Inhaled Anesthetics," *Pharmacotherapy* 18:895-910.

Eger et al. (1995) "Anesthesia by Intravenous Emulsified Isoflurane in Mice," *Can. J. Anesth.* 42:173-176.

El-Aasser et al. (2004) "Miniemulsions: Overview of Research and Applications," *J. Coating Technol. Res.* 1(1):20-31.

Erdlenbruch et al. (2000) "Transient and Controllable Opening of the Blood-Brain Barrier to Cytostatic and Antibiotic Agents by Alkylglycerols in Rats," *Exp. Brain. Res.* 135:417-422.

(56) References Cited

OTHER PUBLICATIONS

Flaim, S.F. (1994) "Pharmacokinetics and Side Effects of Perfluorocarbon-Based Blood Substitutes," *Art. Cells Blood Subs. Immob. Biotech.* 22(4):1043-1054.

Forster et al. (1998) "Applications of Emulsions," In; *Modern Aspects of Emulsion Science*, Binks, B. Ed., The Royal Society of Chemistry: Cambridge, pp. 395-426.

Forrest et al. (2006) "In Vitro Release of the mTOR Inhibitor Rapamycin from Poly(ethylene glycol)-b- poly(ε-caprolactone) Micelles," *J. Controlled Release* 110:370-377.

Franks et al. (1994) "Molecular and Cellular Mechanisms of General Anesthesia," *Nature* 367:607-614.

Franks et al. (1996) "Temperature Dependence on the Potency of Volatile General Anesthetics: Implications for in Vitro Experiments," *Anesthesiology* 84:716-720.

Friberg et al. (1978) "Emulsification and the HLB-Temperature," *J. Colloid Interface Sci.* 66:367-368.

Fujita et al. (1971) "Fluorocarbon Emulsion as a Candidate for Artificial Blood," *Eur. Surg. Res.* 3:436-453.

Gabizon et al. (May 1993) "Prolongation of the Circulation Time of Doxorubicin Encapsulated in Liposomes Containing a Polyethylene Glycol-Derivatized Phospholipid: Pharmocokinetic Studies in Rodents and Dogs," *Pharm. Res.* 10(5):703-708.

Greiner et al. (1993) "Fluorinated Surfactants Intended for Biomedical Uses," In; *Organofluorine Compounds in Medicinal Chemistry and Biomedical Applications*, Filler et al. Eds., Elsevier Science Publishers, pp. 339-380.

Halpern, D.F. (1993) "Recent Developments in Fluorine Substituted Volatile Anesthetics," In; *Organofluorine Compounds in Medicinal Chemistry and Biomedical Applications*, Filler et al. Eds., Elsevier Science Publishers, pp. 101-133.

Hapfelmeier et al. (2001) "Sevoflurane Potentiates and Blocks GABA-Induced Currents Through Recombinant Alpha(1)ss(2)gamma(2) GABA(A) Receptors: Implications for an Enhanced GABAergic Transmission," *Eur. J. Anesthesiology* 18:377-383.

Harris et al. (Mar. 2003) "Effect of Pegylation on Pharmaceuticals," *Nat. Rev. Drug Disc.* 2:214-221.

Higuchi et al. (1962) "Physical Degradation of Emulsions Via the Molecular Diffusion Route and the Possible Prevention Thereof," *J. Pharmaceutical Sci.* 51(5):459-466 *J. Pharm. Sci.* 51(5):459-466.

Hoang et al. (Aug. 31, 2004) "Aqueous Solubilization of Highly Fluorinated Molecules by Semifluorinated Surfactants," *Langmuir* 20(18):7347-7350.

Hoang et al. (2003) "Ostwald Ripening of Alkane in Water Emulsions Stabilized by Hexaethylene Glycol Dodecyl Ether," *Langmuir* 19:6019-6025.

Hoar et al. (1943) "Transparent Water-in-oil Dispersions: The Oleopathic Hydro-Micelle," *Nature* 152:102-103.

Holmgren et al. (1998) "Code for Collagen's Stability Deciphered," *Nature* 392:666-667.

Homgren et al. (1999) "A Hyperstable Collagen Mimic," *Chem. Biol.* 6(2):63-70.

Hung et al. (2006) "Development and Evaluation of Emulsion-Liposome Blends for Reservation Delivery," *J. Nanosci. Nanotechnol.* 6:2950-2958.

International Search Report, Corresponding to International Application No. PCT/US05/00100, Mailed Jul. 12, 2006.

International Search Report and Written Opinion, Corresponding to International Application No. PCT/US07/85710, Mailed Sep. 18, 2008.

Ishida et al. (2004) "Biodistribution Characteristics of Galactosylated Emulsions and Incorporated Probucol for Hapatocyte-Selective Targeting of Pipophilic Drugs in Mice," *Pharm. Res.* 21(6):932-939.

Izquierdo et al. (2002) "Formation and Stability of Nano-Emulsions Prepared Using the Phase Inversion Temperature Method," *Langmuir* 18:26-30.

Jadhav et al. (2006) "Applications of Microemulsion Based Drug Delivery System," *Curr. Drug Deliv.* 3:267-273.

Jafari et al. (2006) "Nano-Emulsion Production by Sonication and Microfluidization—A Comparison," *Int. J. Food. Properties* 9:475-485.

Johannesson et al. (1984) "Halothane Dissolved in Fat as an Intravenous Anesthetic to Rats," *Acta Anaesthesiol Scand.* 28(4):381-384.

Jones et al. (1999) "Polymeric Micelles: A New Generation of Colloidal Drug Carriers," *Eur. J. Pharm. Biopharm.* 48:101-111.

Jones et al. (2003) "Toxicological Perspectives on Perfluorinated Compounds," *Organohalogen. Comp.* 62:311-314.

Kabalnov et al. (1992) "Ostwald Ripening Theory: Applications to Fluorocarbon Emulsion Stability," *Adv. Colloid Interface Sci.* 38:69-97.

Kabalnov et al. (Dec. 1990) "Solubility of Fluorocarbons in Waster as a Key Parameter Determining Fluorocarbon Emulsion Stability," *J. Fluorine. Chem.* 50(3):271-284.

Kabalnov et al. (1996) "Macroemulsion Stability: The Oriented Wedge Theory Revisited," *Langmuir* 12:276-292.

Kalyanasundaram et al. (1976) "Environmental Effects on Vibronic Bans Intensities in Pyrene Monomer Fluorescence and their Application in Studies of Micellar Systems," *J. Am. Chem. Soc.* 99:2039-2044.

Kalyanasundaram, K. (1988) "Pyrene Fluorescence as a Probe of Fluorocarbon Micelles and their mixed Micelles with Hydrocarbon Surfactants," *Langmuir* 4:942-945.

Kawamoto et al. (1992) "Acute Pulmonary Edema After Intravenous Liquid Halothane in Digs," *Anesth. Analg.* 74:747-752.

Kennedy et al. (2004) "The Toxicology of Perfluorooctanoate," *Crit. Rev. Tox.* 34:351-384.

Khan et al. (2006) "Multiple Emulsions: An Overview," *Curr. Drug. Deliv.* 3:429-443.

Kim et al. (2002) "Pharmocokinetic and Pharmocodynamic Evaluation of Cyclosporin A O/W-Emulsion in Rats," *Int. J. Pharmaceutics* 249(1-2):149-156.

Kissa, E. (2001) "Polymeric Fluorinated Surfactants," In; *Fluorinated Surfactants and Repellents*, $2^{nd}$ ed., Surfactant Science Series, vol. 97, Marcel Dekker, Inc. pp. 15-28.

Komori et al. (2007) "Alteration of Therapeutic Efficacy of Lipid Micro Spheres Incorporating Prostaglandin E1 by Mixing with Aqueous Solution," *J. Pharmaceutical Sci.* 96(4):935-943.

Kopriva et al. (1969) "An Anesthetic Accident: Cardiovascular Collapse from Liquid Halothane Delivery," *Anesthesiology* 30:246-247.

Krafft et al. (1998) "Highly Fluorinated Amphiphiles and Colloidal Systems, and Their Applications in the Biomedical Field. A Contribution," *Biochimie* 80:489-514.

Krafft, M.P. (2001) "Fluorocarbons and Fluorinated Amphiphiles in Drug Delivery and Biomedical Research," *Adv. Drug Del. Rev.* 47:209-228.

Krafft et al. (1994) "Supramolecular Assemblies from Single Chain Perfluoroalkylated Phosphorylated Amphiphiless," *Coll. Surf. A* 84:113-119.

Krafft et al. (1991) "Detrimental Effect of Excess Lecithin on the Stability of Fluorocarbon/Lecithin Emulsions," *J. Phys. Chem.* 95:5673-5676.

Krafft, M.P. (2004) "Applications of Fluorous Compounds in Materials Chemistry," *Handbook of Fluorous Chemistry*, Gladysz et al. Eds., Wiley-VCH: Weinheim, Ch. 12, pp. 478-504.

Krasowski et al. (2000) "The Actions of Ether, Alcohol and Alkane General Anesthetics on GABA and Glycine Receptors and the Effects of TM2 and TM3 Mutations," *Brit. J. Pharmacol.* 129:731-743.

Krishna et al. (1993) "Pharmacokinetics, Efficacy and Toxicity of Parenteral Haalofantrine in Uncomplicated Malaria," *Brit. J. Clin. Pharmacol.* 36:585-591.

Krishnadas et al. (Feb. 2003) "Sterically Stabilized Phospholipid Mixed Micelles: In Vitro Evaluation as a Novel Carrier for Water-Insoluble Drugs," *Pharm. Res.* 20(2):297-302.

Kwon et al. (1994) "Block Copolymer Micelles as Vehicles for Hydrophobic Drugs," *Colloids Surf. B. Biointerfaces* 2:429-434.

Kwon, G.S. (2003) "Polymeric Micelles for Delivery of Poorly Water-Soluble Compounds," *Crit. Rev. Ther. Drug Carrier Syst.* 20:357-403.

Kwon et al. (2003) "Polymeric Micelles for the Delivery of Polyene Antibiotics," *Polymeric Mater. Sci Eng.* 89:50-51.

(56) References Cited

OTHER PUBLICATIONS

Lance et al. (1995) "Structure and Toxicity of Amphotericin B/triglyceride Emulsion Formulations," *J. Antimicrob. Chemother.* 36(1):119-128.

Lau et al. (2004) "The Developmental Toxicity of Perfluoroalkyl Acids and their Derivatives," *Tox. Appl. Pharm.* 198:231-241.

Lavasanifar et al. (2001) "Micelles Self-Assembled from Poly(thylene oxide)-bloxkpoly-(N-hexyl stearate L-Aspartamide) by a Solvent Evaporation Method: Effect on the Solubilization and Haemolytic Activity of Amphotericin B," *J. Control. Rel.* 77:155-160.

Lavasanifar et al. (2002) "Poly(ethylene Oxide)-Block-Poly(L-Amino Acid) Micelles for Drug Delivery," *Adv. Drug Del. Rev.* 54:169-190.

Lifshitz et al. (1961) "The Kinetics of Precipitation from Supersaturated Solid Solutions," *J. Phys. Chem. Solids* 19(1-2):35-50.

Liu et al. (2007) "Preparation of Poly(butylene-co-$\epsilon$-caprolactone carbonate) and Their use as Drug Carriers for a Controlled Delivery System," *J. Polym. Sci. A Polym. Chem.* 45(11):2152-2160.

Liu et al. (2006) "Formation and Stability of Paraffin Oil-in-Water Nano-Emulsions Prepared by the Emulsion Inversion Point Method," *J. Colloid Interface Sci.* 303:557-563.

Lixin et al. (2006) "A Less Irritant Norcantharidin Lipid Microspheres: Formulation and Drug Distribution," *Int. J. Pharmaceutics* 323(1-2):161-167.

Lo et al. (1987) "The Disposition and Bioavailability of Intravenous and Oral Nelbuphine in Healthy Volunteers," *J. Clin. Pharmacol.* 27:866-873.

Lukyanov et al. (May 7, 2004) "Micelles from Lipid Derivatives of Water-Soluble Polymers as Delivery Systems for Poorly Soluble Drugs," *Adv. Drug Deliv. Rev.* 56(9):1273-1289.

Madhusudhan et al. (2007) "1-*O*-alkylglycerol Stabilized Carbamazepine Intravenous o/w Nanoemulsions for Drug Targeting in Mice," *J. Drug Targeting* 15(2):154-161.

Martin et al. (2005) "Synthesis and Self-Assembly of Amphiphilic Semifluorinated Calix[4]arenes," *Supramol. Chem.* 17:9-15.

Martin et al. (2005) "Solution Self-Assembly and Solid-State Properties of Fluorinated Amphiphilic Calix[4]arenes," *Chem. Comm.* 39:4964-4966.

Martin et al. (2006) "Synthesis and pH-Dependent Self-Assembly of Semifluorinated Calix[4]arenes," *Tetrahedron* 63(25):5539-5547.

Mason et al. (2006) "Nanoemulsions: Formation, Structure and Physical Properties," *J. Phys. Condens. Matter* 18:R635-R666.

Medina et al. (2001) "Use of Ultrasound to prepare Lipid Emulsions of Lorazepam for Intravenous Injection," *Int. J. Pharmaceutics* 216(1-2):1-8.

Messina et al. (1998) "Perfluorocarbon-Hydrocarbon Self-Assembly. Part 3. Liquid Phase Interactions Between Perfluoroalkylhalides and Heteroatom Containing Hydrocarbons," *Tetrahedron Lett.* 9069-9072.

Miller, C.A. (2006) "Spontaneous Emulsification Recent Developments with Emphasis on Self-Emulsification," In; *Emulsions and Emulsion Stability*, 2nd ed., Sjonlom, J. Ed., Marcel Dekker: New York, 132:107-126.

Monduzzi, M. (1998) "Self-Assembly in Fluorocarbon Surfactant Systems," *Curr. Opin. Coll. Int. Sci.* 3:467-477.

Mosqueira et al. (2006) "Surface-Modified and Conventional Nanocapsules as Novel Formations for Parental Delivery of Halofantrine," *J. Nanosci. Nanotechnol.* 6:3193-3202.

Mosqueira et al. (2004) "Efficacy and Pharmacokinetics of Intravenous Nanocapsule Formulations of Halofantrine in Plasmodium berghei-Infected Mice," *Antimicrobial Agents Chemother.* 48:1222.

Mozzi et al. (2002) "The Use of Lipid Emulsions for the IV Administration of a New Water Soluble Polyene Antibiotic, SPK-843," *J. Antimicrob. Chemother.* 49(2):321-325.

Muller et al. (2004) "SolEmuls—Novel Technology for the Formulation of I.V. Emulsions with Poorly Soluble Drugs," *Int. J. Pharmaceutics* 269(2):293-302.

Mussler et al. (1999) "The Anesthetic and Physiologic Effects of an Intravenous Administration of a Halothane Lipid Emulsion (5% vol./vol.)," *Aneth. Analg.* 88:671-675.

Nakajima, H. (1997) "Microemulsions in Cosmetics," In; *Industrial Applications of Microemulsions*, Solans et al. Eds., Marcel Decker: New York, pp. 175-197.

Neil et al. (2000) "Towards the Nonstick Egg: Designing Fluorous Proteins," *Chem. Biol.* 7:R153-R157.

Norden et al. (2001) "Physiocochemical Characterization of a drug-Containing Phospholipid-Stabilized o/w Emulsion for Intravenous Administration," *Eur. J. Pharmaceutical Sci.* 13(4):393-401.

Oda et al. (2000) "Aggregation Properties and Mixing Behavior of Hydrocarbon, Fluorocarbon, and Hybrid Hydrocarbon-Fluorocarbon Cations Dimeric Surfactants," *Langmuir* 16:9759-9769.

Office Action, Corresponding to U.S. Appl. No. 11/028,948, Mailed Aug. 1, 2008.

Ozpolat et al. (2003) "Pharmacokinetics of Intravenously Administered Liposomal All-Trans-Retinoic Acid (ATRA) and Orally Administered ATRA in Healthy Volunteers," *J. Phram. Pharmaceutical Sci.* 6:292-301.

Palakurthi et al. (2005) "Biodisposition of PEG-Coated Lipid Microspheres of Indomethacin in Arthritic Rats," *Int. J. Pharmaceutics* 290(1-2):55-62.

Percec et al. (2002) "Cell Membrane as a Model for the Design of Semifluorinated Ion-Selective Nanostructures Supramolecular Systems," *Tetrahedron* 58:4031-4040.

Petsev et al. (1995) "Flocculation of Deformable Emulsion Droplets. II Interaction Energy," *J. Colloid Interface Sci.* 176:201-213.

Pohlmann et al. (2002) "Spray-Dried Indomethacin-Loaded Polyester Nanocapsules and Nanospheres Development, Stability Evaluation and Nanotstructure Models," *Eur. J. Pharmaceutical Sci.* 16(4-5):305-312.

Primo et al. (2007) "Binding of Photophysical Studies of Biocompatible Magnetic Fluid in Biological Medium and Development of Magnetic Nanoemulsion: A New Candidate for Cancer Treatment," *J. Magnetism Magnetic Mater.* 310:2838-2840.

Ravey et al. (1988) "Comparative Study of Fluorinated and Hydrogenated Nonionic Surfactants," *Prog. Colloid Poly. Sci.* 76:234-241.

Riess J.G. (2002) "Fluorous Micro- and Nanophases with a Biomedical Perspective," *Tetrahedron* 58:4113-4131.

Riess, J.G. (2004) "Fluorous Materials for Biomedical Uses," In; *Handbook of Fluorous Chemistry*, Wiley-VCH, pp. 521-573.

Riess, J.G. (2001) "Oxygen Carriers (Blood Substitutes)-Raison d'Etre, Chemistry and Some Physiology," *Chem. Rev.* 101:2797-2919.

Riess, J.G. (1994) "Highly Fluorinated Systems for Oxygen Transport, Diagnosis and Drug Delivery," *Colloids Surf. A.* 84:33-48.

Reiss et al. (1992) "Stabilization of Fluorocarbon Emulsions by Sugar-Derived Perffluoroalkylated Surfactants and Co-surfactants," *Prog. Colloid Polym. Sci.* 88:123-130.

Reiss, J.G. (2005) "Understanding the Fundamentals of Perfluorocarbons and Perfluorocarbon Emulsions Relevant to In Vivo Oxygen Delivery," *Artificial Cells Blood Subdtitutes Biotechnol.* 33:47-63.

Rosler et al. (2001) "Advanced Drug Delivery Devices Via elf-Assembly of Amphiphilic Block Copolymers," *Adv. Drug Del. Rev.* 53:95-108.

Salager et al. (1982) "Surfactant-Oil-Water Systems Near the Affinity Inversion. Part I: Relationship Between Equilibrium Phase Behavior and Emulsion Type and Stability," *J. Dispersion Sci. Technol.* 3:279-292.

Sandison et al. (1970) "An Experimental Study of Pulmonary Damage Associated with Intravenous Injection of Halothane in Dogs," *Br. J. Anaesth.* 42:419-423.

Sarker, D.K. (2005) "Engineering of Nanoemulsions for Drug Delivery," *Curr. Drug Deliv.* 2:297-310.

Schmutz et al. (2003) "Fluorinated Vesicles Made from Combinations of Phospholipids and Semifluorinated Alkanes. Direct Experimental Evidence of the Location of Semifluorinated Alkane Within the Bilayer," *Langmuir* 19:4889-1894.

Schulman et al. (1959) "Mechanism of Formation and Structure of Micro Emulsions by Electron Microscopy," *J. Phys. Chem.* 63:1677-1680.

(56) References Cited

OTHER PUBLICATIONS

Seki et al. (2004) "A Nanometer Lipid Emulsion, Lipid Nano-Sphere (LNS), as a Parental Drug Carrier fro Passive Drug Targeting," *Int. J. Pharmaceutics* 273(1-2):75-83.

Sharma et al. (1988) "Novel Compositions of Emulsified Perfluorocarbons for Biological Uses," *Biomat. Art. Cells Art. Org.* 16:447-450.

Shawer et al. (2002) "VLDL-Resembling Phospholipid-Submicron Emulsion for Cholesterol-Based Targeting," *J. Pharmaceutical Sci.* 91(6):1405-1413.

Shinoda et al. (1968) "The Effect of Temperature on the Phase Equilibria and the Types of Dispersions of the Ternary System Composed of Water, Cyclohexane, and Nonionic Surfactant," *J. Colloid Interface Sci.* 26:70-74.

Slaughter et al. (2007) "Synthesis and Self-Assembly Properties of a Novel [poly9ethylene glycol0}-Fluorocarbon-Phospholipid Triblock Copolymer," *Tetrahedron Lett.* 48:3879-3882.

Smart, B.E. "Characteristics of C-F Systems," In; *Organofluorine Chemistry: Principles and Commercial Applications*, Plenum Press, New York, pp. 57-88, 1994.

Smart, B.E. (1983) "Fluorocarbons," In; *The Chemistry of Functional Groups*, Supplement D, John Wiley and Sons, pp. 603-655.

Solans et al. (2003) "Nano-Emulsions: Formation, Properties and Applications," In; *Adsorption and Aggregation of Surfactants in Solution*, Marcel Dekker, Inc.: New York, pp. 525-554.

Solans et al. (2005) "Nano-Emulsions," *Curr. Opin. Colloid Interface Sci.* 10:102-110.

Strippoli et al. (2000) "Anticandidal Activity of SPA-S-843, a New Polyenic Drug," *J. Antomicrob. Chemother.* 45:235-237.

Sutton et al. (1971) "Accidental Intravenous Injection of Halothane," *Br. J. Anaest.* 43:513-519.

Swanson et al. (1953) "Ultra-Short-Acting Thiobarbituric Acids," *Proc. Soc. Exp. Biol. Med.* 82:212-215.

Tadros et al. (2004) "Formation and Stability of Nano-Emulsions," *Adv. Colloid Interface Sci.* 108-109:303-318.

Tang et al. (2001) "Stabilization of Coiled-Coil Peptide Domains by Introduction of Trifluoroleucine," *Biochemistry* 40:2790-2796.

Taylor, P. (1998) "Ostwald Ripening in Emulsions," *Adv. Colloid Interface Sci.* 75:107-163.

Taylor, P. (2003) "Ostwald Ripening in Emulsions. Estimation of Solution Thermodynamics of the Disperse Phase," *Adv. Colloid Interface Sci.* 106:261-285.

Teixeira et al. (2005) "Development and Characterization of PLGA Nanospheres and Nanocapsules Containing Xanthone and 3-Methoxyxanthone," *Eur. J. Pharmaceutics Biopharmaceutics* 59:491-500.

Thurmond et al. (1999) "Shell Cross-Linked Polymer Micelled: Stabilized Assemblies with great Versatility and Potential," *Coll. Surf B* 16:45-54.

Tiwari et al. (2006) "Preparation and In Vitro Characterization of Multifunction nanoemulsions for Simultaneous MR Imaging and Targeted Drug Delivery," *J. Biomed. Nanotechnol.* 2:217-224.

Torchilin, V.P. (2001) "Structure and Design of Polymeric Surfactant-Based Drug Delivery Systems," *J. Controlled Release* 73:137-172.

Ueda et al. (2004) "Prolonged Circulation of Menatetrenone by Emulsions with Hydrogenated Castor Oils in Rats," *J. Controlled Release* 95(1):93-100.

van Etten et al. (Nov. 1995) "Sterically Stabilized Amphotericin B-Liposomes: Toxicity and Biodistribution in Mice," *J. Controlled Release* 37(1-2):123-129.

Vierling et al. (Feb. 2001) "Highly Fluorinated Amphiphiles as Drug and Gene Carrier and Delivery Systems," *J. Fluorine Chem.* 107(2):337-354.

Wang et al. (2006) "Submicron Lipid Emulsion as a Drug Delivery System for Nalbuphine and Its Prodrugs," *J. Controlled Release* 115(2):140-149.

Watkins et al. (1993) "*Falciparum* Malaria: Differential Effects of Antimalarial Drugs on Ex Vivo Parasite Viability During the Critical Early Phase of Therapy," *Am. J. Trop. Med. Hygiene* 49:106.

Weers et al. (1994) "The Effect of Molecular Diffusion on Initial Particle Size Distributions in Phospholipid-Stabilized Fluorocarbon Emulsions," *Colloids Surf. A Physiochem. Eng. Aspects* 84:81-87.

Wu et al. (1996) "Potentiation by Sevoflurane of the γ-Aminobutyric Acid Induced Chloride Current in Acutely Dissociated CA1 Pyramidal Neurons from Rat Hippocampus," *Brit. J. Pharmaco.* 119:1013-1021.

Xue et al. (1997) "Perfectly Staggered and Twisted Difluorormethylsene Groups in Perfluoroalkyl Chains; Structure of $M[C_4F_9SO_2NSO_2C_4F_9]$ (M=Na, K)," *Angew. Chem. Int Ed. Engl.* 36:1331-1333.

Yeeprae et al. (2005) "Biodistribution Characteristics of Mannosylated and Fucosylated O/W Emulsions in Mice," *J. Drug Targeting* 13(8):479-487.

Yeeprae et al. (2006) "Effect of Mannose Density on Mannose Receptor-Mediated Cellular Uptake of Mannosylated O/W Emulsions by Macrophages," *J. Controlled Release* 114(2):193-201.

Yu et al. (2001) "mTOR, a Novel Target in Breast Cancer: The Effect of CCO-779, an mTOR Inhibitor, in Preclinical Models of Breast Cancer," *Endocrine-Related Cancer* 8:249-258.

Zalipsky, S. (1993) "Synthesis of an End-Group Functionalized polyethylene glycol-Lipid Conjugate for Preparation of Polymer-Grafted Liposomes," *Bioconj. Chem.* 4(4):296-299.

Zarif et al. (1993) "Alkyl and Perfluooalkyl Glycolipid-Based Supramolecular Assemblies," *Coll. Surf. A* 84:107-112.

Zhang et al. (1996) "Development of Amphiphilic Diblock Copolymers as Micellar Carriers of Taxol," *Int. J. Pharmaceutics* 132:195-206.

Zhou et al. (2006) "The Efficacy and Safety of Intravenous Emulsified Isoflurane in Rats," *Anesth. Analg.* 102:129-134.

Zimmerman et al. (1994) "Potentiation of $GABA_A$ Receptor Cl⁻ Current Correlates with in Vivo Anesthetic Potency," *J. Pharmacol. Experim. Ther.* 270:987-991.

\* cited by examiner

SEMI-FLUORINATED BLOCK COPOLYMERS FOR DELIVERY OF THERAPEUTIC AGENTS

CROSS-REFERENCE TO RELATED APPLICATIONS

This application claims priority under 35 U.S.C. 119(e) to U.S. provisional Patent Application 60/884,672 filed Jan. 12, 2007, which is hereby incorporated by reference in its entirety.

STATEMENT REGARDING FEDERALLY SPONSORED RESEARCH OR DEVELOPMENT

This invention was made with United States government support awarded by the following agencies: ARMY/MRMC Grant no. W81XWH-05-1-0478 and NSF Grant no. 0518112. The United States has certain rights in this invention.

BACKGROUND OF INVENTION

Self assembled nanostructures are a class of materials having chemical and physical properties attractive for drug formulation, administration and delivery applications. Amphiphilic polymer micelle supramolecular structures, for example, are capable of encapsulating and facilitating the solubilization of poorly water soluble drugs, including extremely hydrophobic pharmaceutical compositions. Encapsulation of drugs by amphiphilic polymer self assembled micelle nanostructures also has benefits for reducing toxicity and stabilizing therapeutic agents under administration and delivery conditions. Incorporation of targeting ligands into amphiphilic polymer micelle delivery systems also has potential for enabling directed delivery of pharmaceuticals to specifically targeted cells, tissues and organs.

Amphiphilic polymer micelles are formed via entropically driven self assembly processes of amphiphilic polymers, including block copolymers, having spatially segregated hydrophilic and hydrophobic domains. For example, when amphiphilic polymers are provided in aqueous solution at a concentration above critical micelle concentration (CMC) the polymers aggregate and self align such that hydrophobic domains form a central hydrophobic core and hydrophilic domains self align into an exterior hydrophilic corona region exposed to the aqueous phase. The core-corona structure of amphiphilic polymer micelles provides useful physical properties, as the hydrophobic core provides a shielded phase capable of solubilizing hydrophobic molecules, and the exterior corona region is at least partially solvated, thus imparting colloidal stability to these nanostructures. Amphiphilic polymer micelles typically exhibit a spherical geometry and may have substantially uniform nanoscale cross sectional dimensions ranging from about 10 nanometers to about 100 nanometers. These physical dimensions are large enough to allow for effective loading and stabilization of hydrophobic molecules, such as drugs, into the hydrophobic core of amphiphilic polymer micelles. Amphiphilic polymer micelle nanostructures are small enough, however, to allow their effective circulation in the blood for prolonged periods. Micelle compositions are also subject to low mononuclear phagocyte uptake and low levels of renal excretion. In addition, amphiphilic polymers of these structures are typically small enough so that upon dissociation of the micelles they are effectively eliminated by the kidney, thus avoiding potentially deleterious buildup of micelle components in the liver. As a result of this combination of attributes, amphiphilic polymer micelles are rapidly emerging as a preferred class of nanomaterials for delivering low-solubility, highly hydrophobic drugs, such as anti-cancer drugs, and antifungal agents.

A number of amphiphilic polymers, including block copolymers, have been specifically designed and developed for drug delivery and formulation applications. The following references provide examples of amphiphilic polymer drug delivery systems, including block copolymer drug delivery systems, which are hereby incorporated by reference in their entireties; Kwon, G. S.; Naito, M.; Kataoka, K.; Yokoyama, M.; Sakurai, Y.; Okano, T. "Block Copolymer Micelles as Vehicles for Hydrophobic Drugs" Colloids and Surfaces, B: Biointerfaces 1994, 2, 429-34; Torchilin, V. P. "Structure and Design of Polymeric Surfactant-Based Drug Delivery Systems" J. Controlled Release 2001, 73, 137-172; Kwon, G. S. "Polymeric Micelles for Delivery of Poorly Water-Soluble Compounds" Crit. Rev. Ther. Drug Carrier Syst. 2003, 20, 357-403; Adams, M. L.; Lavasanifar, A.; Kwon G. S. "Amphiphilic Block Copolymers for Drug Delivery" J. Pharm. Sci. 2003, 92, 1343-1355; Jones, M. -C.; Leroux J. -C.; "Polymeric Micelles: A New Generation of Colloidal Drug Carriers" Eur. J. Pharm. Biopharm. 1999, 48, 101-111; 36. Burt, H. M.; Zhang, X.; Toleikis, P.; Embree, L.; Hunter, W. L. "Development of Copolymers of poly(D,L-lactide) and Methoxypolyethylene Glycols as Micellar Carriers of Paclitaxel" Coll. Surf. B Biointerfaces. 1999, 16, 161-171; Lavasanifar, A.; Samuel, J.; Kwon G. S. "Poly(ethylene oxide)-block-poly(L-amino acid) Micelles for Drug Delivery"". Adv. Drug Del. Rev. 2002, 54, 169-190; and Lavasanifar, A.; Samuel, J.; Kwon G. S. "The Effect of fatty Acid Substitution on the in vitro Release of Amphotericin B from Micelles Composed of poly(ethylene oxide)-block-poly(N-hexyl stearate-L-aspartamide" J. Control Release 0.2003, 87, 23-32).

Poly(ethylene glycol) (PEG) is a widely used hydrophilic, corona-forming segment. PEG-based amphiphilic polymers developed for drug delivery including PEG-poly($\epsilon$-caprolactone), PEG-poly(amino acid), PEG-polylactide and a variety of a PEG—phospholid constructs, such as PEG-distearoylphosphatidylethanolamine. Use of PEG-containing amphiphilic polymers has been demonstrated to have a number of significant benefits. First, PEG is considered to have biocompatible properties and its incorporation in amphiphilic polymer micelles confers lower toxicity to these nanostructures. Second, incorporation of a PEG hydrophilic component into amphiphilic polymer micelle nanostructures has been shown to reduce uptake by the reticuloendothelial system. Finally, PEG hydrophilic segments are capable of conjugation to a variety of different hydrophobic polymers via a number of conventional synthetic pathways. Other hydrophilic groups portions have been pursued for enhancing amphiphilic polymer micelle stability including cross linked systems, such as use of a cross linked poly(acrylic acid) corona component [Thurmond, K. B.; Huang, H. Y; Clark, C. G.; Kowalewski, T.; Wooley, K. L. Coll. Surf. B. 1999.16, 45-54] and use of a cross linked poly(amino acid) corona component [U.S. Pat. Pub. No. 2006/0240092].

Despite significant advances in the development of micelle delivery systems significant challenges remain that limit clinical adoption of this technology. In vivo stability is an important factor for effective micellar drug delivery. Micelles experience conditions of extreme dilution upon intravenous delivery that often reduces the concentration of block copolymers to well below critical micelle concentration. Such dilution consequently initiates rapid dissociation of the micelles, thereby resulting in loss of therapeutic cargo prior to delivery to cells and tissue of interest. Accordingly, the critical micelle concentration of amphiphilic polymers for micelle delivery systems is of great importance to effective clinical implementation. In addition, interactions with blood components, such as proteins, lipids and carbohydrates, can also destabilize micelles under in vivo conditions. These interactions can result in loss and/or premature release of therapeutic cargo outside the targeted region, thereby reducing the efficiency or rendering ineffective micelle drug delivery systems. To address these challenges, several strategies to mitigate premature dissociation of the micelles have been pursued.

Modifications of the hydrophobic segment of the amphiphilic polymer can induce a radical change in the assembly behavior of the micelle. For instance, attaching two hydrophobic chains to the same end of the hydrophilic segment is known to have the potential of generating a bilayer that can eventually close into a vesicle. This is a commonly observed case for phospholipids when the hydrophilic section of the amphiphile is of comparable size to the phospholipid. Vesicles or liposomes are very stable, but they can be ten times bigger than micelles, and difficult to functionalize. They can also create problems in the mechanisms of excretion from the organism in which they are injected. More importantly, the interior of a liposome is not hydrophobic as both the external and internal surfaces of such an aggregate are lined with hydrophilic groups.

Other approaches for stabilizing micelle systems for drug delivery include formulations having stabilizing additives, such as stabilizers, surfactants and excipients. Additives for enhancing micelle stability may be capable of integrating into hydrophilic and/or hydrophobic regions of the micelle structure so as enhance stability during delivery, for example by reducing the extent of destabilization by protein-micelle interactions.

A more common strategy for stabilizing micelles consists of using hydrophobic segments that contain functional groups able to interact, and therefore bind, the encapsulated drug. Examples of substituted hydrophobic segments pursued for micelle drug delivery applications include poly(β-substituted aspartate), poly(γ-substituted glutamate) and poly (L-leucine). While this approach can be effective in some specific cases, it should be noted that functionalization of the hydrophobic segment of an amphiphilic molecule often results in a significant decrease in its hydrophobicity, therefore increasing the critical micelle concentration. Accordingly, a trade-off exists in the functionalization of hydrophilic portions of amphiphilic polymers for micelle drug delivery between achieving effective molecular recognition/drug binding and retaining a degree of hydrophobicity necessary for stable micelle-mediated drug delivery. As a consequence, micelles that are able to encapsulate and deliver specific compounds are currently limited in number and only work for very specific compounds under relatively narrow delivery conditions.

U.S. Patent Publication US2005/0214379 (Mecozzi et al.) published on Sep. 29, 2005 describes an alternative approach wherein a block copolymer having a perfluorinated or semifluorinated block is used for micelle drug delivery. As reported by the authors, fluorination, particularly perfluorination, can have a significant impact on the physical and chemical properties of organic molecules. Incorporation of a perfluorinated component to a block copolymer, for example, can result in formation of a fluorous phase, that does not readily mix with both polar and/or non-polar hydrogenated phases. Perfluorinated polymers also have a low surface energy, they are both lipo- and hydrophobic, and they are often unsurpassed in their high chemical and thermal stabilities. Applicability of the disclosed perfluorinated or semifluorinated block copolymers for encapsulation and administration of a variety of fluorine containing therapeutic compositions, including sevoflurane, is reported in Mecozzi et al. In an embodiment, block copolymers having a perfluorinated block are provided at a concentration larger than the critical micelle concentration so as to form stable supramolecular structures capable of encapsulating fluorophilic chemical compounds. The authors report that the fluorinated or perfluorinated block copolymers self assemble into micelles wherein the fluorinated or semifluorinated blocks of the copolymer orient toward and surround a fluorous core of the fluorine containing therapeutic composition. A variety of block copolymer compositions are reported as useful for administration of fluorinated therapeutic compositions, including dual block copolymers having a poly(ethylene glycol) block and a perfluorinated alkane block.

U.S. patent application Ser. No. 11/946,174, filed on Nov. 28, 2007, describes formulations capable of generating a nanoemulsion of a large amount of a fluorinated volatile anesthetic dispersed in an aqueous solution. Formulations of this reference include surfactants, such as semi-fluorinated block copolymers having a hydrophilic block and a fluorophilic block that are capable of self-assemble upon emulsification to form supramolecular structures dispersed in an aqueous continuous phase that encapsulate and stabilize significant quantities of the fluorinated volatile anesthetic component in a fluorous inner droplet core. The formulations in U.S. patent application Ser. No. 11/946,174 also include one or more stabilizing additives, such as one or more perhalogenated fluorocarbons, that enhance stability with respect to droplet size by decreasing the rate of Ostwald ripening, coagulation and/or phase separation processes.

It will be appreciated from the foregoing that polymer compositions for micelle delivery systems are needed for the administration and formulation of insoluble and/or toxic pharmaceutical compositions. Micelle delivery systems and formulations providing enhanced stability under delivery conditions are required for a variety of clinical applications. Amphiphilic polymers exhibiting a low critical micelle concentration, low toxicity and a high degree of biocompatibility are needed to enable practical implementation of micelle mediated drug delivery.

SUMMARY OF THE INVENTION

The present invention provides semi-fluorinated block copolymers and related methods of synthesizing and using semi-fluorinated block copolymers for drug administration and delivery and drug formulation applications. Semi-fluorinated block copolymers of this aspect of the invention include block copolymers having discrete hydrophilic, fluorophilic and hydrophobic structural domains that are capable of forming supramolecular structures in aqueous solutions, such as micelles, for encapsulating hydrophobic and/or fluorophilic therapeutic agents. Encapsulation by semi-fluorinated block copolymers of the present invention allows for enhanced solubilization, protection and stabilization of hydrophobic and/or fluorophilic therapeutic agents relative to conventional drug delivery compositions and methods. Semi-fluorinated block copolymers of the present invention, and formulations thereof, enable intravenous administration and delivery of a range of therapeutic compositions, including sparingly soluble, hydrophobic drugs, such as anticancer drugs, and fluorophilic therapeutic compositions, such as anesthetics and fluorinated steroids. Optionally, semifluorinated block copolymers of the present invention are capable of functionalization to provide targeted delivery of micelle encapsulated drugs to specific cells, tissues and/or organs.

Semi-fluorinated block copolymers of the present invention, for example, provide micelle nanostructures for drug delivery that exhibit a high degree of stability and biocompatibility under clinically relevant drug formulation, administration and delivery conditions. In an embodiment, for example, a semi-fluorinated block copolymer micelle of the present invention comprises an amphiphlic block copolymer comprising an intermediate fluorophilic structural domain conjugated to, and positioned between a hydrophilic block and a hydrophobic group of the copolymer. Inclusion of this fluorophilic component is useful for enhancing the overall thermokinetic stability of drug encapsulating micelle nanostructures formed by self assembly relative to conventional micelle nanostructures comprising amphiphilic polymers having only hydrophilic and hydrophobic groups. For example, incorporation of the intermediate fluorophilic domain is useful for providing amphiphilic block copolymers having a low critical micelle concentration in aqueous solution. This attribute of the present semifluorinated block copolymers is useful for forming drug encapsulating micelle nanostructures exhibiting stability under extreme dilution conditions encountered upon intravenous administration of therapeutic formulations. Semi-fluorinated block copolymers of the present invention also enhance micelle stability with respect to potential disruption and/or dissociation induced by interactions with reactive blood components, such as proteins, lipids and carbohydrates.

Polymers, block copolymers, micelle nanostructures and related formulations of this aspect of the present invention provide a high degree of versatility, as the composition of the fluorophilic block component (e.g. length of the fluorophilic block, number of carbon-fluorine bonds, etc.) can be selectively adjusted to: (i) access lower critical micelle concentrations and enhance stability under delivery conditions, (ii) control the kinetics of release of the encapsulated therapeutic (e.g., provide faster or slower release rates), and (iii) enhance the stability of therapeutic formulations under storage conditions (e.g., increase shelf life). Incorporation of a fluorophilic polymer component in the present invention, therefore, provides delivery systems wherein the release rate characteristics of therapeutic agents can be deterministically controlled (or "tuned") via selection of the composition, structure, and size of the fluorophilic domain, thereby enabling a versatile class of drug delivery nanostructures capable of providing a range of useful release characteristics including rapid release, slow release and sustained release.

In one aspect, the present invention provides a therapeutic formulation for delivering a hydrophobic or fluorophilic therapeutic agent to a patient comprising: the therapeutic agent and a plurality of semi-fluorinated polymers. The formulation of this aspect optionally further comprises an aqueous solution. In an embodiment, the semi-fluorinated polymers of the present therapeutic formulation are block copolymers comprising a hydrophilic block, a fluorophilic block, and a hydrophobic group; wherein the fluorophilic block of each of the semi-fluorinated block copolymers is positioned between the hydrophilic block and the hydrophobic group. As used herein, the term formulation refers to compositions prepared for a desired therapeutic use, such as delivery of a therapeutic agent or combination of therapeutic agents. Formulations of the present invention may be in a form ready for administration to a subject or may be provided in a form that requires one or more additional steps prior to administration to a subject. Formulations of the present invention include aqueous solutions containing supramolecular structures for administering and/or delivering therapeutic agents, such as micelles encapsulating therapeutic agents, and also include precursor compositions for preparing therapeutic aqueous formulations.

Fluorophilic blocks of copolymers of the present invention may be directly conjugated to the hydrophilic block and the hydrophobic group. Direct conjugation of polymer blocks (e.g., hydrophilic blocks, fluorophilic blocks) and groups (e.g., hydrophobic groups) has the benefit in some applications of not adversely affecting micelle stability and biocompatibility. Alternatively, the present invention includes semifluorinated block copolymers wherein fluorophilic blocks are linked to hydrophobic groups and/or hydrophilic blocks via one or more linking groups. A wide variety of linking groups are useful for conjugating polymer blocks and functional groups of the semi-fluorinated polymers of the present invention including, but not limited to, alkyl groups, alkenyl groups, carbonyl groups, ester groups, amide groups, phosphate groups, disulfide groups or any combinations or derivatives of these linking groups. Use of linking groups for conjugating adjacent polymer blocks (e.g., hydrophilic blocks, fluorophilic blocks) and/or functional groups (e.g., hydrophobic groups) that do not substantially reduce the stability and/or biocompatibility of drug encapsulating supramolecular structures, such as micelles, formed by self assembly of the present semifluorinated block copolymers are preferred for some applications. Semifluorinated block copolymers of the present invention also include polymers and block copolymers having a plurality of hydrophilic blocks, hydrophobic groups and/or fluorophilic blocks.

In some embodiments, semi-fluorinated block copolymers comprise amphiphilic semi-fluorinated copolymers capable of self assembly in aqueous solution to form supramolecular structures for at least partially encapsulating one or more therapeutic agents. Useful semi-fluorinated block copolymers of the present invention include, but are not limited to, amphiphilic block copolymers capable of self assembly into micelle nanostructures encapsulating hydrophobic and/or fluorophilic therapeutic agents. A supramolecular micelle structure of the present invention, for example, has an interior hydrophobic core comprising the hydrophobic groups of the semi-fluorinated block copolymers, an intermediate fluorophilic portion comprising fluorophilic blocks of the semi-fluorinated block copolymers and an exterior hydrophilic portion comprising hydrophilic blocks of the semi-fluorinated block copolymers; wherein the hydrophilic portion is separated from the hydrophobic core by the intermediate fluorophilic portion. The encapsulated therapeutic agent may be localized in the hydrophobic core, intermediate fluorophilic portion or in both the hydrophobic core and the intermediate fluorophilic portion of the supramolecular structure. Micelles formed by semifluorinated block copolymers of the present invention are particularly attractive for drug delivery applications given their long circulation times, biocompatibility and ability to achieve a useful extent of drug loading, solubilization and encapsulation. In some embodiments, semifluorinated block copolymers of the present invention self assemble to form supramolecular structures, such as micelle nanostructures, having cross sectional physical dimensions (e.g., diameter etc.) selected over the range of about 10 nanometers to about to about 100 nanometers. Supramolecular nanostructures of the present invention having cross sectional dimensions less than about 200 nm are beneficial in some drug delivery applications for avoiding immune response, lowering potential toxicity and decreasing the rate of filtering by interendothelial cells slits at the spleen. The present invention includes, however, semifluorinated block copolymers capable of generating supramolecular nanostructures and microstructures other than micelles including, but not limited to, vesicles, bilayers, and folded sheets.

In an embodiment, the fluorophilic block of the semi-fluorinated copolymer is a fluorinated alkyl chain, such as a perfluorinated alkyl chain, semifluorinated alky chain, perhalogenated alky chain and/or saturated fluorinated or perfluorinated alkyl chain. Exemplary fluorinated alkyl chains of fluorophilic blocks of copolymers of the present invention may be straight (e.g., unbranched) or branched, and in some embodiments have chain lengths selected over the range of about 6 to about 20 carbons. In some embodiments, the degree of fluorophilicity of a fluorophilic block is selectively controlled by incorporation of a fluorocarbon segment having a number of carbon-fluorine bonds selected from the range of about 12 to about 40 carbon-fluorine bonds. For some drug delivery applications, the composition, structure, length and/or number of carbon-fluorine bonds of a fluorinated alkyl chain, optionally a perfluorinated alkyl chain, of the fluorophilic block is selected so as to selectively control (i.e., to "tune") the critical micelle concentration of the semi-fluorinated polymers and/or release properties of the therapeutic formulation for a given clinical application.

Useful hydrophilic blocks in copolymers of this embodiment include polyoxigenated polymer blocks, such as a poly(ethylene glycol) block having a molecular weight selected over the range of about 1000 g mol$^{-1}$ to about 12,000 g mol$^{-1}$. In some embodiments, poly(ethylene glycol) blocks of semi-fluorinated block copolymers of the present invention are long enough to provide therapeutic agent encapsulated micelle delivery structures having solubilities and biocompatibilities useful for a range of clinical settings, including intravenous delivery of therapeutic agents. PEG hydrophilic blocks of semi-fluorinated block copolymers of the present invention may be functionalized, for example via incorporation of targeting ligands for directed delivery applications, or via cross linking between PEG components of copolymers to enhance micelle stability. Although a PEG hydrophilic group is preferred in some block copolymers, the present invention includes semifluorinated block copolymers having a hydrophilic group other than PEG, such as polyesters, polyamides, polyanhydrides, polyurethanes, polyimines, hydrophilic polypetides, polyureas, polyacetals, polysaccharides and polysiloxanes.

Semi-fluorinated block copolymers of the present invention may comprise hydrophobic groups having a range of compositions, chemical properties and physical properties. Selection of the composition of the hydrophobic group may be based on a number of factors including; (i) the composition and physical properties of the therapeutic agent to be encapsulated, formulated and/or delivered, (ii) on the basis of general micelle stability and thermodynamic considerations, and/or (iii) on the basis of the available synthetic pathways and linking chemistry for conjugating hydrophobic groups and fluorophilic blocks of the block copolymers. In one embodiment, the hydrophobic group is a phospholipid group. Use of a hydrophobic group comprising a glycerophospholipid having at least one hydrophobic alkyl chain having a length of about 12 to about 24 carbons, such as a distearoyl-glycero-phosphoethanolamine, is attractive for some drug delivery applications as it is capable of encapsulating and/or binding to highly hydrophobic molecules, including a number of important anti-cancer therapeutics, so as to provide therapeutic formulations comprising drug delivery micelles having an extent of therapeutic agent loading acceptable for clinical application. In addition, phospholipid hydrophobic groups are beneficial in semifluorinated block copolymers of the present invention because they are capable of effective conjugation with a fluorophilic block comprising a fluorinated alkyl chain, optionally a perfluorinated alkyl chain. Hydrophobic groups of semifluorinated block copolymers of the present invention may be cross linked so as to enhance micelle stability. The present invention includes, however, block copolymers having a hydrophobic group other than a phospholipid group, such as a poly(lactic acid) polymer block, poly(propylene glycol) polymer block; a poly(amino acid) polymer block; a poly(ester) block; or a poly (ε-caprolactone) polymer block.

Selection of the composition of the hydrophobic group of semi-fluorinated block copolymers of the present invention can also be made on the basis of the composition of the therapeutic agent component. Therapeutic formulations having certain hydrophobic group and therapeutic agent combinations, for example, exhibit enhanced stability, biocompatibility, controlled release properties, solubility and low toxicity. Compositions of the present invention include the following specific combinations of the therapeutic agent and hydrophobic group of the semi-fluorinated block copolymers: (1) Paclitaxel and poly(lactic acid), (2) Rapamycin and poly(caprolactone), (3) 17-AAG and poly(lactic acid) and (4) Amphotericin B and phospholipid.

In an aspect, the present invention provides semi-fluorinated block copolymers for forming supramolecular structures capable of encapsulating therapeutic agents, wherein the block copolymers have the chemical formula:

wherein n is selected from the range of 20 to 240, and m is selected from the range of 6 to 20;

wherein R1 is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group.

wherein [Hydrophobic group] is the hydrophobic group of the semi-fluorinated block copolymers;

wherein L$_1$ is a first linking group selected from the group consisting of an alkyl group, alkenyl group, carbonyl group, ester group, amide group, phosphate group, disulfide group and any combination of these, and wherein x equals 0 or 1; and wherein L$_2$ is a second linking group selected from the group consisting of an alkyl group, alkenyl group, carbonyl group, ester group, amide group, phosphate group, disulfide group and any combination of these, and wherein y equals 0 or 1.

Useful alkoxy R1 groups in some applications include, but are not limited to, methoxy group (CH$_3$O).

In an embodiment particularly useful for the formulation and delivery of hydrophobic therapeutic agents, such as anti-cancer drugs, semifluorinated block copolymers of the present invention have the chemical formula:

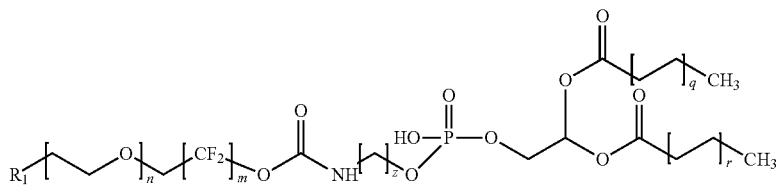

wherein n is selected from the range of 20 to 240, and m is selected from the range of 6 to 20;

wherein R1 is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group;

wherein z is selected from the range of 1 to 10, wherein q is selected from the range of 11 to 23, and r is selected from the range of 11 to 23.

Incorporation of a fluorophilic block into copolymers of the present invention provides supramolecular structures having a fluorous phase, in addition to the hydrophilic corona and hydrophobic core phases, that confers a number of benefits for use of these nanostructures for drug formulation, administration and delivery. First, interactions been fluorophilic block of copolymers comprising a self assembly drug encapsulating supramolecular nanostructure effectively seals or stabilizes the hydrophobic core, thereby providing enhanced stabilization and protection of the therapeutic compositions localized in the core. The self assembled micelle structure represents a dynamic equilibrium, thus, "sealing the hydrophobic core" refers to intermolecular interactions involving the fluorophilic block that enhances the overall thermokinetic stability of the micelle suprastructure, thereby reducing the extent of or preventing unwanted migration of encapsulated therapeutic agents out of the hydrophobic core of the micelle. This sealing effect also lowers the critical micelle concentration of the semifluorinated block copolymers, thereby enhancing the stability of the present drug encapsulating supramolecular nanostructures under delivery conditions. In an embodiment, semifluorinated block copolymers of the present invention have a critical micelle concentration equal to or less than about 1 µM. Second, incorporation of the fluorophilic block allows for selective modulation of the rate of release of therapeutic agents from the present drug encapsulating supramolecular nanostructures. For example, incorporation of a fluorophilic block comprising a perfluorinated alkyl chain having a larger chain length may result in formation of drug encapsulating supramolecular nanostructures exhibiting slower release rates upon administration than a fluorophilic block comprising a perfluorinated alky chain having a smaller chain length. This aspect of the present invention provides an ability to synthetically engineer nanostructures having selected release characteristics, including sustained release. Third, incorporation of a fluorophilic block does not significantly increase the toxicity or removal rates of the present drug encapsulating supramolecular nanostructures relative to conventional micelle delivery systems formed by amphiphilic polymers having PEG hydrophilic and phospholipid hydrophobic groups.

Semifluorinated block copolymer and related drug encapsulating supramolecular nanostructures of the present invention are capable of solubilizing, formulating and delivering therapeutic agents useful in a number of medical and veterinary applications. Useful applications include the delivery of hydrophobic pharmaceuticals for the treatment of cancer, such as paclitaxel, rapamycin, geldanamycin, doxorubicin or any derivatives or prodrugs of these, and for the delivery of substantially toxic anti-fungal agents, such as amophotericin-B. The present polymer compositions and micelle structures, for example, are useful for encapsulating a single type of hydrophobic and/or fluorophilic therapeutic agents or mixtures comprising a plurality of different hydrophobic and/or fluorophilic therapeutic agents. This aspect of the invention is particularly attractive for applications in combination drug therapies.

In an embodiment, therapeutic agents are functionalized prior to formulation and delivery by incorporation of a fluorophilic group, tag or tail, such as a fluorinated or perfluorinated alkyl chain, capable of molecular recognition/associative interaction with the fluorophilic block of the present semifluorinated block copolymers. Incorporation of a fluorophilic group, tail or tag may have benefits of providing enhanced solubilization, stabilization and protection to therapeutic agents encapsulated by the present semi-fluorinated block copolymers. In an embodiment, a fluorophilic group is incorporated into a therapeutic agent via a biocleavable linker, such that upon release the fluorophilic group or tag is removed from the therapeutic agent. In an embodiment, for example, a tag or tail comprising a semi-fluorinated alkyl chain, optionally perfluorinated alkyl chain, is incorporated into the therapeutic agent.

Optionally, therapeutic formulations of the present invention may further comprise one or more additives for enhancing stability of the present supramolecular nanostructures, improving drug-carrier compatibility, increasing drug loading and/or increasing release time. Useful additives include one or more stabilizing additives, pharmaceutically acceptable surfactants, carriers, excipients and preservatives.

Semifluorinated block copolymers of the present invention are suitable for forming supramolecular structures that are useful in a range of other applications in addition to drug delivery applications. Exemplary application of the present semifluorinated block copolymers and related supramolecular structures include encapsulation and formulation of flavoring agents, pigments, and agricultural chemicals such as fungicides and insecticides.

In another aspect, the present invention provides a method of administering a hydrophobic or fluorophilic therapeutic agent to a patient in need of treatment comprising the steps of: (i) providing a therapeutic formulation comprising the therapeutic agent and semi-fluorinated block copolymers in an aqueous solution, wherein each of the semi-fluorinated block copolymers comprises a hydrophilic block, a fluorophilic block, and a hydrophobic group; wherein the fluorophilic block of each of the semi-fluorinated block copolymers is positioned between the hydrophilic block and the hydrophobic group; and (ii) delivering the therapeutic formulation to the patient. Therapeutic formulations of the present invention may be administered in a variety of forms including, but not limited to, as aqueous solutions, colloidal suspensions, emulsions, or combinations of these. Therapeutic formulations of the present invention are capable of administration by a variety of means well known in the art including intravenous administration, topical administration, absorption, transdermal delivery, or oral delivery. Optionally, the present methods include embodiments wherein the length of the fluorinated or perfluorinated alkyl chain is selected so as to control the release rate of the therapeutic agent to the patient, for example to provide a rapid release rate or a slow release rate of the therapeutic agent to the patient.

In another aspect, the present invention provides a method of solubilizing a hydrophobic or fluorophilic therapeutic agent comprising the steps of: providing the therapeutic agent and semi-fluorinated block copolymers in an aqueous solution, wherein each of the semi-fluorinated block copolymers comprises a hydrophilic block, a fluorophilic block, and a hydrophobic group; wherein the fluorophilic block of each of the semi-fluorinated block copolymers is positioned between the hydrophilic block and the hydrophobic group; and wherein semi-fluorinated block copolymers self assemble in aqueous solution to form a supramolecular structure that at least partially encapsulates the therapeutic agent, thereby solubilizing the therapeutic agent.

In another aspect, the present invention provides a method of decreasing the toxicity of a hydrophobic or fluorophilic therapeutic agent comprising the steps of: providing the therapeutic agent and semi-fluorinated block copolymers in an aqueous solution, wherein each of the semi-fluorinated block copolymers comprises a hydrophilic block, a fluorophilic block, and a hydrophobic group; wherein the fluorophilic block of each of the semi-fluorinated block copolymers is positioned between the hydrophilic block and the hydrophobic group; and wherein semi-fluorinated block copolymers self assemble in aqueous solution to form a supramolecular structure that at least partially encapsulates the therapeutic agent, thereby decreasing the toxicity of the therapeutic agent.

In a method of the present invention, the fluorophilic block is a fluorocarbon having has between about 12 to about 40 carbon-fluorine bonds. In a method of the present invention, the fluorophilic block is a fluorinated alkyl chain. In a method of the present invention, the fluorophilic block is a fluorinated alkyl chain having a length of about 6 to about 20 carbons, optionally a perfluorinated alkyl chain having a length of about 6 to about 20 carbons. In a method of the present invention, the length of the fluorinated or perfluorinated alkyl chain is selected so as to control the release rate of the therapeutic agent to the patient, for example, so as to provide a rapid release rate, slow release or sustained release rate of the therapeutic agent to the patient. Semi-fluorinated block copolymers useful in methods of the present invention may have a range of compositions as described above and throughout this application. Methods of the present invention are useful for formulating, solubilizing, administering and/or delivering a range of therapeutic agents, including hydrophobic drugs such as paclitaxel, rapamycin, geldanamycin, doxorubicin, amophotericin-B or any derivatives or prodrugs thereof, and including hydrophobic drugs functionalized via the addition of a fluorophilic group.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
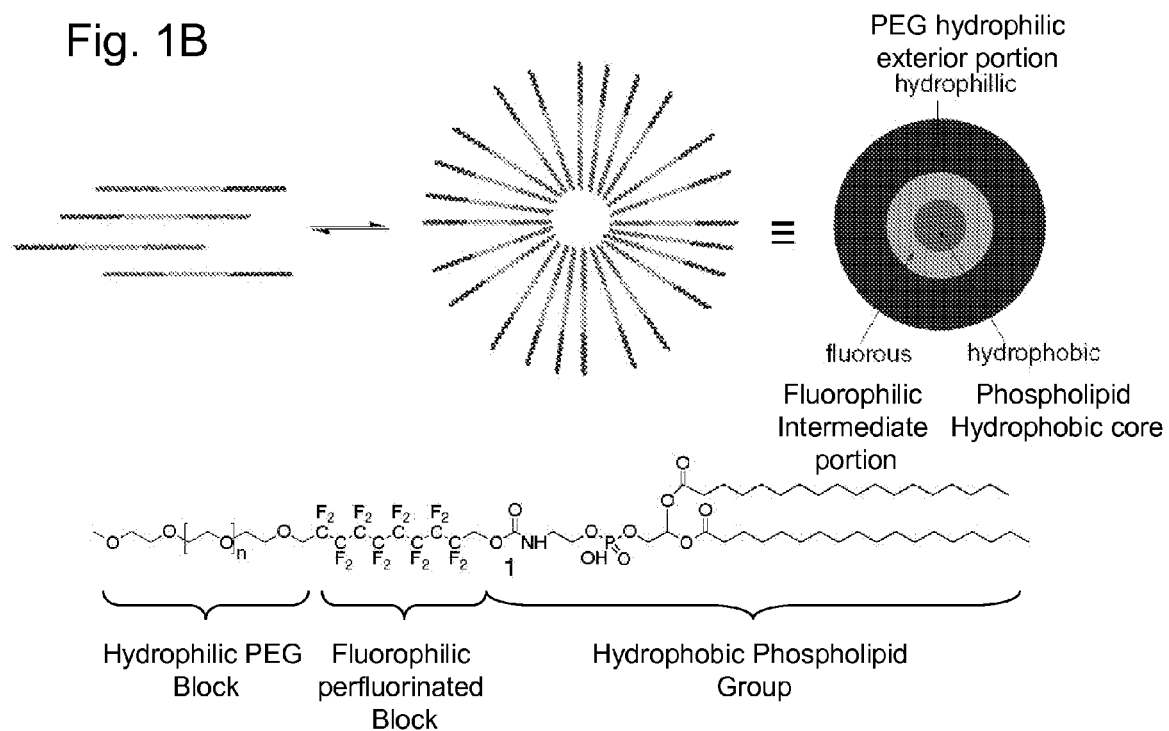
FIG. 1A shows the chemical formula of a semifluorinated block copolymer of the present invention useful for forming drug encapsulating micelles.
FIG. 1B provides a schematic diagram illustrating self assembly of the present semifluorinated block copolymers into a micelle nanostructure capable of encapsulating therapeutic agents.

In general the terms and phrases used herein have their art-recognized meaning, which can be found by reference to standard texts, journal references and contexts known to those skilled in the art. The following definitions are provided to clarify their specific use in the context of the invention.

"Supramolecular structure" refers to structures comprising an assembly of molecules. Supramolecular structures include assemblies of molecules, such as amphiphilic polymers, including block copolymers having a hydrophilic block, fluorophilic block and hydrophobic group, optionally a hydrophobic block. In some supramolecular structures of the present invention, hydrophilic portions of the copolymers are oriented outward toward a continuous aqueous phase and form a hydrophilic corona phase, hydrophobic portions of the copolymers are oriented inward and form a hydrophobic inner core, and fluorophilic portions of the copolymers assemble to form an intermediate fluorous phase positioned between of the hydrophilic and hydrophobic phase of the supramolecular structure. Supramolecular structures of the present invention include, but are not limited to, micelles, vesicles, tubular micelles, cylindrical micelles, bilayers, folded sheet structures, globular aggregates, ripened micelles, and encapsulated droplets. Supramolecular structures of the present invention include self assembled structures. Supramolecular structures may comprise the dispersed phase of a colloid, such as an emulsion or nanoemulsion.

"Semi-fluorinated" refers to chemical compounds having at least one fluorine atom, for example molecules having at least one carbon-fluorine bond.

"Fluorocarbons" refer to chemical compounds that contain at least one carbon-fluorine bond.

"Perfluorinated" and "perfluorocarbon" refer to chemical compounds that are analogs of hydrocarbons wherein all hydrogen atoms in the hydrocarbon are replaced with fluorine atoms. Perfluorinated molecules can also contain a number of other atoms, including bromine, chlorine, and oxygen. A bromine substituted perfluorocarbon is a perfluorocarbon wherein one or more of the fluorine atoms have been replaced with a bromine atom. A chlorine substituted perfluorocarbon is a perfluorocarbon wherein one or more of the fluorine atoms have been replaced with a chlorine atom. A chlorine and bromine substituted perfluorocarbon is a perfluorocarbon wherein one or more of the fluorine atoms have been replaced with a chlorine atom and wherein one or more of the fluorine atoms have been replaced with a bromine atom.

"Polymer" refers to a molecule comprising a plurality of repeating chemical groups, typically referred to as monomers. A "copolymer", also commonly referred to as a "heteropolymer", is a polymer formed when two or more different types of monomers are linked in the same polymer. "Block copolymers" are a type of copolymer comprising blocks or spatially segregated domains, wherein different domains comprise different polymerized monomers. Block copolymers may further comprise one or more other structural domains, such as hydrophobic groups (e.g., phospholipid group). In a block copolymer, adjacent blocks are constitutionally different, i.e. adjacent blocks comprise constitutional units derived from different species of monomer or from the same species of monomer but with a different composition or sequence distribution of constitutional units. Different blocks (or domains) of a block copolymer may reside on different ends or the interior of a polymer (e.g. [A][B]), or may be provided in a selected sequence ([A][B][A][B]). "Diblock copolymer" refers to block copolymer having two different chemical blocks. The term block copolymer includes block copolymers having additional functional groups including, but not limited to hydrophobic groups. The present invention includes novel compositions comprising an amphiphilic block copolymer having a hydrophilic block, fluorophilic block and hydrophobic group, wherein the fluorophilic block is positioned between and conjugated to the hydrophilic block and the hydrophobic group of the polymer. For example, the present invention includes a block copolymer comprising a PEG block, perfluorinated alkane block and phospholipid group, wherein the perfluorinated alkane block is positioned between and conjugated to the hydrophilic PEG block and the hydrophobic phospholipid group of the polymer.

Polymers of the present invention include block copolymers having a first block comprising a larger polymer such as a PEG polymer having 20 to 270 monomers, a second block comprising a smaller polymer (e.g., 2 to 30 monomers), such as a fluorocarbon, including but not limited to, a fluorocarbon such as a fluorinated or perfluorinated alkane, and a hydrophobic group comprising a phospholipid group, such as a glycerophospholipid. Block copolymers of the present invention are capable of undergoing self assembly to make supramolecular structures, including micelle nanostructures for encapsulating therapeutic agents. As used herein, the term block copolymer includes compositions comprising a first block comprising a PEG polymer conjugated to a second fluorophilic block comprising a perfluorinated or semifluorinated molecular domain, such as a perfluorinated or semifluorinated alkane or a perfluorinated or semifluorinated tail, and a third hydrophobic group also conjugated to the second fluorophilic block. As used herein, the term block copolymer also includes functionalized block copolymers, such as a copolymer having functional groups in addition to hydrophobic groups, including ligands, for targeting a supramolecular structure to specific cells, tissues and/or organs, and linking groups for linking a fluorophilic block with a hydrophilic block and a hydrophobic group.

As used herein "hydrophilic" refers to molecules and/or components (e.g., functional groups, blocks of block polymers etc.) of molecules having at least one hydrophilic group, and "hydrophobic" refers to molecules and/or components (e.g., functional groups of polymers, and blocks of block copolymers etc.) of molecules having at least one hydrophobic group. Hydrophilic molecules or components thereof tend to have ionic and/or polar groups, and hydrophobic molecules or components thereof tend to have nonionic and/or nonpolar groups. Hydrophilic molecules or components thereof tend to participate in stabilizing interactions with an aqueous solution, including hydrogen bonding and dipole-dipole interactions. Hydrophobic molecules or components tend not to participate in stabilizing interactions with an aqueous solution and, thus often cluster together in an aqueous solution to achieve a more stable thermodynamic state. In the context of block copolymers of the present invention, a hydrophilic block is more hydrophilic than a hydrophobic group of an amphiphilic block copolymer, and a hydrophobic group is more hydrophobic than a hydrophilic block of an amphiphilic polymer.

As used herein "fluorophilic" refers to molecules and/or components (e.g., functional groups, blocks of block polymers etc.) of molecules having at least one fluorophilic group. A fluorophilic group is one that is capable of participating in stabilizing interactions with a fluorous phase. Fluorophilic groups useful in block copolymers of the present invention include, but are not limited to, fluorocarbon groups, perfluorinated groups and semifluorinated groups.

In the context of the present invention the term patient is intended to include a subject such as an animal. Patient includes a mammal, for example a human subject. Patient includes a subject undergoing a medical procedure, such as undergoing the administration of anesthesia or other medical procedure.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, and cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl group and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.
- —SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
- —OCOOR where R is an alkyl group or an aryl groups;
- —SO$_2$N(R)$_2$ where R is a hydrogen, an alkyl group, or an aryl group and R and R can form a ring;
- —OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

The present invention provides block copolymers and therapeutic formulations of block copolymers, for delivering fluorinated therapeutic compounds, including hydrophobic and/or fluorophilic pharmaceuticals. Supramolecular delivery systems, including micelle delivery systems, are provided for encapsulating, stabilizing and delivering hydrophobic and/or fluorophilic substances to active sites in an organism. In an embodiment, the present approach is based on increasing the stability of micelle delivery nanostructures by incorporating a fluorophilic domain comprising a fluorinated block, such as a perfluorinated chain, into an amphiphilic polymer having hydrophilic and hydrophobic domains. This strategy has several advantages. Interactions between fluorophilic blocks of the copolymer assembled into a drug encapsulating micelle nanostructure act to stabilize the supramolecular structure, thereby lowering the critical micelle concentration. Further, interactions between fluorophilic blocks of the copolymer effectively seal the encapsulated therapeutic agent thereby enhancing its solubilization, protection and stabilization.

EXAMPLE 1

Synthesis and Self-assembly Properties of a [Poly(Ethylene Glycol)]-Fluorocarbon-phospholipid Copolymers for Micelle-based Drug Delivery 1.a. Introduction This Example provides a description of the synthesis of a novel poly(ethylene glycol)-fluorocarbon-phospholipid conjugate that self-assembles into hyper-stable micelles characterized by an internal fluorous phase. Physical characterization of the micelles formed by this polymer in aqueous solution is included. Dynamic light scattering (DLS) measurements indicate a mean diameter of 15 nm (±3 nm), while pyrene fluorescence studies show a critical micelle concentration (CMC) of only 0.65 µM.

1.b. Experimental Results and Discussion

Amphiphilic block copolymers that assemble into micelles in aqueous solutions have found several applications in drug delivery. Biocompatible micelles can be used to solubilize, stabilize, and deliver pharmaceutical agents. The use of micelles is advantageous due to their unique hydrophobic inner core that can sequester sparingly soluble hydrophobic molecules. These nanoparticles can find use in drug delivery for highly hydrophobic drugs, for drugs that are not very stable under physiological conditions, and as a tool to direct delivery to specific tissues or organs. Polymeric micelles with phospholipid or poly-amino acid core blocks have been shown to encapsulate pharmaceuticals such as doxorubicin, amphotericin-B, and paclitaxel. Also, they have been shown to preferentially accumulate in the leaky vasculature of cancerous tumors due to their relatively small size (under 100 nm). Polymeric PEG-based micelles exhibit potential as delivery vessels for pharmaceuticals by likely overcoming obstacles such as poor water solubility of drug candidates, drug bioavailability, and other harmful side-effects via encapsulation of hydrophobic compounds in the micelle inner core hydrophobic environment.

Although micelles have the potential for sustained release formulations, the issue of micelle stability in vivo has yet to be fully resolved so that they may see broad applicability in the area. In order for a micelle to realize potential as a delivery vessel, it must be stable in the presence of blood proteins, such as albumin. Unfortunately, many micelles do not satisfy this condition. Also, the ability of a micelle to maintain its integrity when diluted in vivo is an important factor. Micelles formed from PEG-lipid conjugates are characterized by CMCs on the order of $10^{-5}$ M and half-lives in the blood stream between 1.2 Compositions of the present invention address the problem of the in vivo stability of phospholipid conjugates by designing a novel block copolymer that includes a perfluorinated group between the water solubilizing PEG and the phospholipid (See, FIG. 1).

A perfluorinated group has peculiar physical and chemical properties. It is both hydrophobic and lipophobic at the same time. As a matter of fact, perfluorocarbons prefer to form a separated fluorous phase rather than mix with either hydrophilic or hydrophobic molecules. This phenomenon, known as the fluorophobic effect, allows the self-assembly of highly fluorinated molecules in strict analogy to the hydrophobic effect. In the case of polymer 1, the resulting micelles become stabilized by two different effects. The internal phospholipid forms a classical hydrophobic inner core while the intermediate fluorocarbon assembles with the corresponding perfluorocarbon chains from vicinal polymer molecules to generate an intermediate fluorous shell that contributes to the stability of the micelle and protects a drug encapsulated in the inner core. The advantage of using semi-fluorinated polymers in drug delivery is multifold: (i) It allows the formation of hyperstable micelles due to a combination of hydrophobic and fluorophobic effects. (ii) It allows more direct control of the rate of delivery through the size of the fluorocarbon. (iii) It allows better protection of the encapsulated pharmaceutical. (iv) It confers exceptional resistance to micellar dissociation induced by binding to blood proteins. Therefore, this new approach combines the usefulness of micellar delivery with the flexibility of rational design that can control both the rate of release and the stability of the micelles.

The use of fluorinated surfactants for biomedical purposes has been explored extensively for liposomes and vesicles. Recently, micelles formed by a semi-fluorinated diblock copolymer have been shown to encapsulate highly fluorinated molecules such as volatile anesthetics. In the design of molecule 1, we are taking advantage of the ability of perfluorocarbons to self-assemble in aqueous solutions to generate a PEG-fluorocarbon-phospholipid conjugate that can form hyper-stable micelles with the potential of encapsulating classical hydrophobic drugs.

FIG. 1A shows the chemical formula of a semifluorinated block copolymer of the present invention useful for forming drug encapsulating micelles. The block polymer shown in FIG. 1A is a poly (ethylene glycol) monomethyl ether-fluorocarbon-DSPE conjugate. As shown in this figure, the block copolymer comprises a hydrophilic PEG block, a fluorophilic perfluorinated block and a hydrophobic phospholipid group, wherein the fluorophilic perfluorinated block is conjugated to, and positioned between, the hydrophilic PEG block and the hydrophobic phospholipid group.

FIG. 1B provides a schematic diagram illustrating self assembly of the present semifluorinated block copolymers into a micelle nanostructure capable of encapsulating therapeutic agents. Referring to FIG. 1B, hydrophobic phospholipid groups orient toward the interior of the micelle and form a hydrophobic core. The PEG hydrophilic blocks orient toward the exterior and form a hydrophilic corona component of the micelle that undergoes stabilizing interactions with the aqueous solution. The fluorophilic perfluorinated blocks self align to form an intermediate fluorous phase positioned between the hydrophilic corona phase and the hydrophobic core phase. In some embodiments, therapeutic agents are localized to the hydrophobic core and/or fluorous phases of the micelle nanostructure.

Polymer 1, composed of a monomethylated [poly(ethylene glycol)] characterized by an average molecular weight of 5000 g/mol, a perfluorooctyl group, and the phospholipid 1,2-distearoyl-S,N-glycero-3-phosphoethanolamine (DSPE) has been synthesized through a five-step synthesis. Preliminary characterization of micelles formed from the tri-block conjugate shows a mean diameter of 15 nm (±3 nm) and a critical micelle concentration (CMC) of 0.65 mM. This is a considerably lower CMC than that of the analogous PEG-DSPE conjugate (6.2 mM).

Design of the mPEG-fluorocarbon-lipid conjugate 1 was modeled on earlier PEG-lipid conjugates. Polyethylene glycol (PEG) is by far the most common choice for the hydrophilic component of micelles and liposomes. Its behavior is well studied both in vitro and in vivo, and it is one of the few polymers approved by the FDA for use in cosmetics and pharmaceuticals. PEG is known to lack immunogenicity, and it has been shown that pegylation of liposomes increases the half life, decreases drug leaking, and decreases uptake by the reticuloendothelial system.

The phospholipid DSPE was chosen because it is known to assist in encapsulation of compounds such as the anticancer drugs doxorubicin and paclitaxel as well as the toxic fungicide amphotericin-B. Its use in the synthesis of PEG-lipid conjugates for the assembly into micelles is well established.

Synthesis of the mPEG-fluorocarbon-DSPE conjugate 1 is described in Scheme 1. Initially, the hydroxyl functionality of mPEG (MW=5000 g/mol) was activated by reaction with methanesulfonyl chloride in dichloromethane at room temperature to give compound 2 (90%). Subsequently, 2,2,3,3,4,4,5,5,6,6,7,7,8,8,9,9-hexadecafluorodecane-1,10-diol was mono-protected with benzyl bromide using crushed KOH in N,N-dimethylformamide at room temperature to give benzyl ether 3 (90%). To ensure that mono- versus di-protection was favored, the perfluorinated diol was used in a 3:1 excess during the reaction. A trace amount of di-protected material was detected by thin-layer chromatography, but this by-product was easily separated from the desired mono-protected diol via flash column chromatography. The mono-protected alcohol 3 was coupled to the activated mPEG 2 using an excess of sodium hydride in refluxing tetrahydrofuran to give the benzyl-protected mPEG-hexadecafluorodecanol 4. After quenching with water, the reaction mixture was filtered to remove salts. Isolation of PEG derivatives is often accomplished by precipitation of the hydrophilic polymer from a mixture of solvents. In this specific case, a solution of tetrahydrofuran and cold diethyl ether was used to isolate intermediate conjugate 4, which was carried on to the next step without further purification. Hydrogenolysis of 4 removed the benzyl group and yielded the corresponding de-protected alcohol 5. The alcohol was activated with an excess of N,N'-disuccinimidyl carbonate (DSC) to give the desired succinimidyl derivative 6. $^1$H NMR showed a signal for un-reacted

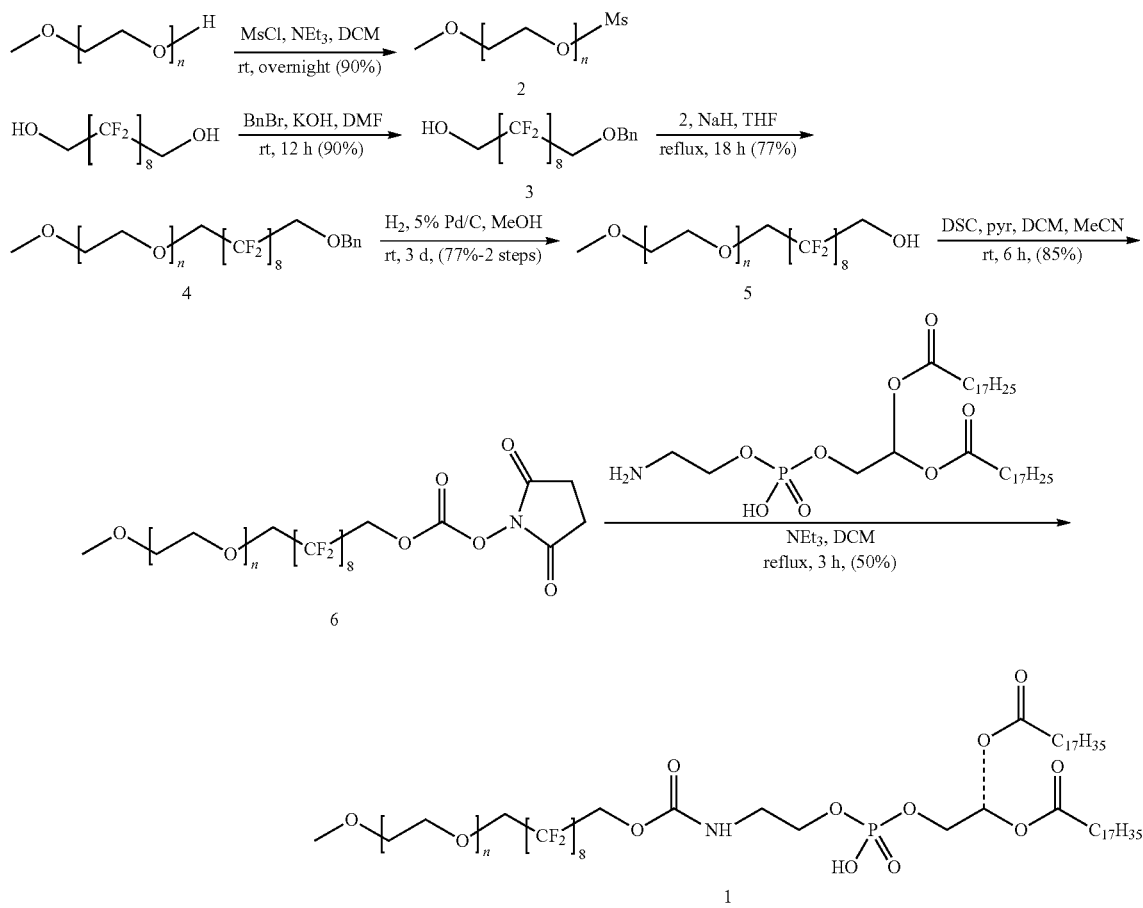

Scheme 1. Synthesis of poly(ethylene glycol) monomethyl ether-fluorocarbon-DSPE conjugate (1).

DSC at 2.65 ppm (<10%). In order to remove the excess DSC, the mixture was dissolved in acetone and the product precipitated by adding diethyl ether. A slight excess of 1,2-distearoyl-sn-glycero-3-phospho-ethanolamine (DSPE) and triethylamine was used in an attempt to drive the coupling of 5 to the lipid. The excess amine was removed by quenching with acetic acid, followed by removal of dichloromethane in vacuo. Any excess lipid was removed by taking up the remaining residue in water and filtering out the resulting solids. The filtrate was lyophilized to give a white fluffy solid. HPLC analysis of the solid indicated that a minor amount (<15%) of PEG-perfluoroalkyl conjugate 4 was still present. The mixture was purified by preparative HPLC using a Jordi-Gel reverse phase divinylbenzene column (500 Å 22×100 mm).

In an embodiment, a five-step synthesis is employed to make the novel poly (ethylene glycol)-fluorocarbon-phospholipid conjugates that self-assembles into hyper-stable micelles characterized by an internal fluorous phase. The synthesis requires coupling of an activated monomethyl [poly (ethylene glycol)] (mPEG) to 10-(benzyloxy)-2,2,3,3,4,4,5,5,6,6,7,7,8,8,9,9-hexadecafluorodecan-1-ol. After hydrogenolysis of the benzyl protecting group a reactive succinimidyl carbonate group is installed in order to facilitate coupling of the resulting mPEG-hexadecafluorodecanol with 1,2-distearoyl-S,N-glycero-3-phosphoethanolamine (DSPE).

Figure 3:
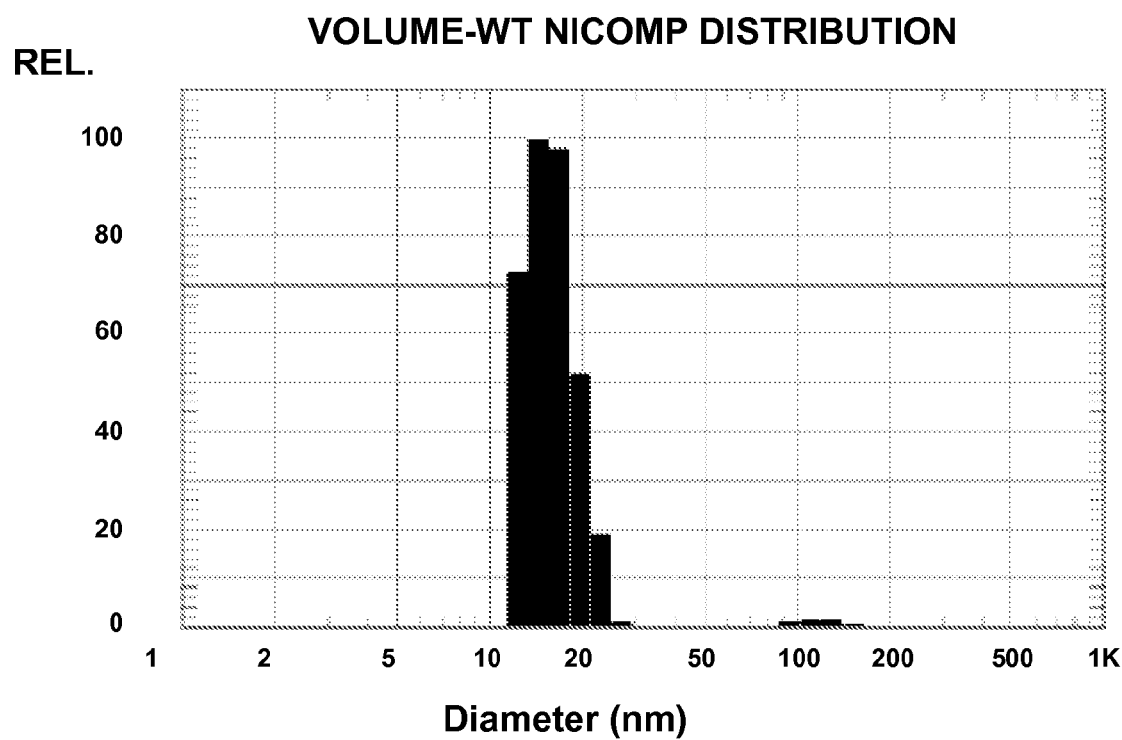
FIG. 3. Volume-weighted distribution obtained by NICOMP analysis, showing a mean diameter of 15 nm (+3 nm) for micelles of the present invention.

The mean diameter of the micelles formed by the polymer in aqueous solutions was measured using dynamic light scattering (DLS). FIG. 3 illustrates the volume-weighted distribution obtained by NICOMP analysis, showing a micellar mean diameter of 15 nm (±3 nm).

Figure 2:
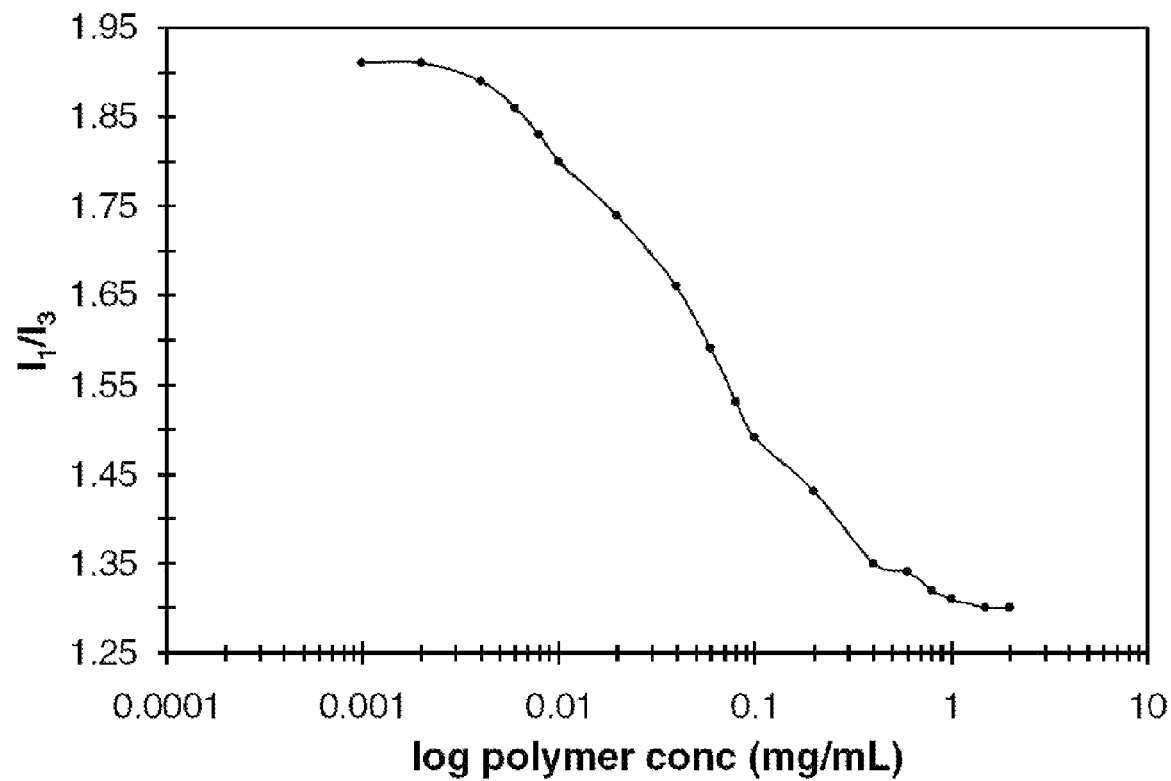
FIG. 2. Change in ratio of the intensities ($I_1/I_3$) of the first to the third peaks in the vibronic fluorescence spectrum of pyrene at different polymer concentrations. From this plot, the critical micelle concentration (CMC) was determined to be 0.65 µM by taking the first point where the curve becomes non-linear.

Pyrene is often used to determine the onset of aggregation in micelles. According to the py scale, the ratio of the intensities (I1/I3) of the first to the third peaks in the vibronic fluorescence spectrum of pyrene depends on the polarity of the environment. In water, this ratio is approximately 1.87 and in hexanes it is approximately 0.58. FIG. 2 illustrates the change in I1/I3 intensity with changing of the polymer concentration. From this plot of I1/I3 versus co-polymer concentration of the CMC was determined to be 0.65 mM by taking the first point where the curve becomes non-linear.

In summary, we have successfully synthesized a novel poly-(ethylene glycol)-fluorocarbon-lipid conjugate 1 capable of self-assembling into micelles with a lower CMC than analogous PEG-lipid conjugates. This physical characterization demonstrates increased stability of the micelles, which supports the use of these micelles as delivery vessels for sparingly soluble pharmaceuticals.

1.c. Experimental Section
General Methods and Materials.

$^1$H and $^{19}$F NMR spectra were recorded on a Varian $^{UNITY}$ INOVA 400 MHz spectrometer using a Varian QN switchable BB probehead. $^{13}$C NMR were recorded on a Varian $^{UNITY}$ INOVA 500 MHz spectrometer using a Nalorac QN DD probehead. Chemical shifts (d) were reported in parts per million (ppm) relative to trimethyl silane (TMS). Coupling constants (J) were reported in hertz (Hz). The initial polydispersed mPEG (MW 5000) was purchased from Fluka (Buchs, Switzerland) and was dissolved in water and lyophilized before use. The phospholipid distearoyl phosphatidylethanolamine (DSPE) was purchased from Avanti Polar Lipids, Inc. (Alabaster, Ala.). All other chemicals were purchased from Sigma-Aldrich (Milwaukee, Wis.). N,N'-Disuccinimidyl carbonate purchased from Sigma-Aldrich was recrystallized in ethyl acetate to remove N-hydroxysuccinimide impurities. Anhydrous solvents were obtained through a Seca Solvent System by Glass Contour (Laguna Beach, Calif.). Water used for the DLS and the CMC determinations was filtered through a Millipore® system (Molsheim, France). HPLC was conducted on a manual injection Gilson HPLC with a 321 pump system and a Gilson prep-ELS detector. The columns were Jordi Gel reverse phase divinylbenzene (500 Å) 4.6×150 mm (analytical) or 22×100 mm (prep). Fluorescence spectra were obtained with a F3010 Hitachi fluorometer. Micellar size was determined from dynamic light scattering on Zeta Potential/Particle Sizer Nicomp 380 ZLS, and data was interpreted using NICOMP analysis with the particle sizes expressed as volume weighted average diameter in nanometers (nm).

List of Abbreviations

Tetrahydrofuran (THF); monomethylated [poly (ethylene glycol)] MW=5000 g/mol (mPEG); diethyl ether (Et$_2$O); N,N-dimethylformamide (DMF); ethyl acetate (EtOAc); dichloromethane (DCM); acetonitrile (MeCN); pyridine (pyr); N,N'-disuccinimidyl carbonate (DSC); 1,2-distearoyl-S,N-glycero-3-phosphoethanolamine (DSPE)

Monomethyl-poly (ethylene glycol) methanesulfonate (2)

A dry 250 mL round bottom flask was charged with mPEG (0.4 mmol, 1.98 g) and anhydrous dichloromethane (15 ml). Triethylamine (4.0 mmol, 0.56 ml) and methanesulfonyl chloride (2.6 mmol, 0.2 ml) were added and the reaction mixture was stirred overnight under argon at room temperature. The reaction mixture was concentrated in vacuo and taken up in chloroform. The precipitated salts were removed by gravity filtration and by running filtrate through silica gel. The collected product was concentrated in vacuo, dissolved in water and lyophilized to yield a white powder (90%). $^1$H NMR (CDCl$_3$): δ 4.38 (m, 2H), 3.47-3.82 (m, PEG-H), 3.38 (s, 3H), 3.09 (s, 3H); $^{13}$C NMR (CDCl$_3$): δ 72.0, 70.7, 69.37, 69.1, 59.1, 37.8.

10-(benzyloxy)-2,2,3,3,4,4,5,5,6,6,7,7,8,8,9,9-hexadecafluorodecan-1-ol (3)

A dry 5 mL round bottom flask was charged with 2,2,3,3,4,4,5,5,6,6,7,7,8,8,9,9-hexadecafluorodecane-1,10-diol (2.2 mmol, 1.0 g), dry DMF (2.5 mL), and crushed potassium hydroxide (2.2 mmol, 121 mg). The mixture was flushed with argon and benzyl bromide (0.7 mmol, 123 mg) was added dropwise over 15 minutes. The solution was allowed to stir overnight at room temperature under argon. The reaction mixture was concentrated in vacuo, and the residue was partitioned between aqueous saturated ammonium chloride and ethyl acetate. The aqueous layer was extracted twice with EtOAc. The organic layers were combined, washed with water then brine, dried over MgSO$_4$, and concentrated in vacuo. The residue was purified via flash column chromatography on silica gel using 5% EtOAc in petroleum ether as the eluent. The product was isolated as colorless oil; upon drying under high vacuum for 12 h, the oil solidified (90%). $^1$H NMR (CDCl$_3$): δ7.36 (m, 5H), 4.68 (s, 2H), 4.10 (td, 2H, J=14, 6), 3.94 (t, 2H, J=14), 1.96 (t, 1H, J=7); $^{13}$C NMR (CDCl$_3$): δ136.6, 128.8, 128.5, 128.0, 74.7, 66.9, 60.9; $^{19}$F NMR (CDCl$_3$): δ −119.8, −122.3, −122.8, −123.7, −123.9.

10-[poly(ethylene glycol) mono-methyl ether]-2,2,3,3,4,4,5,5,6,6,7,7,8,8,9,9-hexadecafluorodecane-1-ol (5)

A dry 250 mL round bottom flask was charged with 2 (0.09 mmol, 467 mg), 10-(benzyloxy)-2,2,3,3,4,4,5,5,6,6,7,7,8,8, 9,9-hexadecafluorodecan-1-ol 3 (0.28 mmol, 153 mg), and anhydrous THF (50 mL). The mixture was flushed with argon, and excess NaH was added. The resulting mixture was warmed to reflux and allowed to stir under argon for 18 h. The reaction mixture was cooled to room temperature and quenched with about 10 drops of water. The salts were removed via gravity filtration, and the resulting filtrate was concentrated in vacuo. The residue was dissolved in THF and the PEG-derivative was precipitated by adding diethyl ether. The resulting solid was filtered and transferred to a dry 100 mL round bottom flask. Methanol (20 mL) and an excess of 5% Pd/C were added. The suspension was flushed and purged three times with hydrogen, and the resulting reaction mixture was allowed to stir under hydrogen atmosphere at room temperature for three days. The mixture was filtered over a pad of celite, and the filtrate was concentrated in vacuo. The resulting residue was taken up in THF and $Et_2O$ was added to precipitate a solid. The suspension was refrigerated for about 30 minutes to ensure complete precipitation, and the flaky, cream-colored solid (77%) was collected via vacuum filtration. $^1$H NMR ($CDCl_3$): δ 4.05 (m, 4H), 3.4-3.8 (m, PEG-H), 3.38 (s, 3H); $^{13}$C NMR ($CDCl_3$): δ 72.5, 72.1, 70.92, 70.9, 70.7, 68.5, 60.5, 59.2; $^{19}$F NMR ($CDCl_3$): δ −120.1, −122.2, −122.4, −123.6, −123.8.

Poly (ethylene glycol) monomethyl
ether-fluorocarbon-succinimidyl carbonate (6)

A dry 5 mL round bottom flask was charged with 5 (0.09 mmol, 500 mg), DCM (0.5 mL), MeCN (0.1 mL), pyr (0.1 mL), and DSC (0.90 mmol, 237 mg). The reaction mixture was allowed to stir at room temperature for 6 h under argon. Solvents were removed in vacuo, and the resulting residue was taken up in acetone [about 10 mL] and $Et_2O$ [about 40 mL] was added to precipitate a creamy solid. The suspension was refrigerated for about 30 minutes, and the cream-colored solid was collected via vacuum filtration (85%). $^1$H NMR ($CDCl_3$): δ 4.78 (t, 2H, J=13), 4.04 (t, 2H, J=14), 3.4-3.8 (m, PEG-H), 3.38 (s, 3H), 2.87 (s, 4H); $^{13}$C NMR ($CDCl_3$): δ 168.04, 151.21, 72.44, 72.06, 70.84, 70.78, 70.68, 68.41, 64.99, 59.15, 25.54; $^{19}$F NMR ($CDCl_3$); δ −120.1, −122.2, −122.4, −123.6, −123.8.

Poly (ethylene glycol) monomethyl
ether-fluorocarbon-DSPE conjugate (1)

A dry 50 mL round bottom flask was charged with 6 (0.4 mmol, 2.20 g), DSPE (0.8 mmol, 590 mg), and 25 mL dry DCM. The mixture was flushed with argon and triethylamine (1.0 mmol, 0.15 ml) was added. The reaction mixture was heated to reflux and stirred for 3 h under argon. The mixture was cooled, diluted with 0.15 ml glacial acetic acid, and concentrated in vacuo. The residue was taken up in 5 mL water and filtered to remove a white solid. The filtrate was lyophilized to give a white fluffy solid, which was purified by prep-HPLC (50%). $^1$H NMR ($CDCl_3$): δ4.72 (t, 2H, J=13), 4.04 (t, 2H, J=14), 3.4-3.8 (m, PEG-H), 3.38 (s, 3H), 1.59 (m, 4H), 1.25 (s, 50H), 0.88 (t, 3H, J=6.8); $^{19}$F NMR ($CDCl_3$): δ −120.1, −120.3, −122.3, −123.8.

Figure 4:
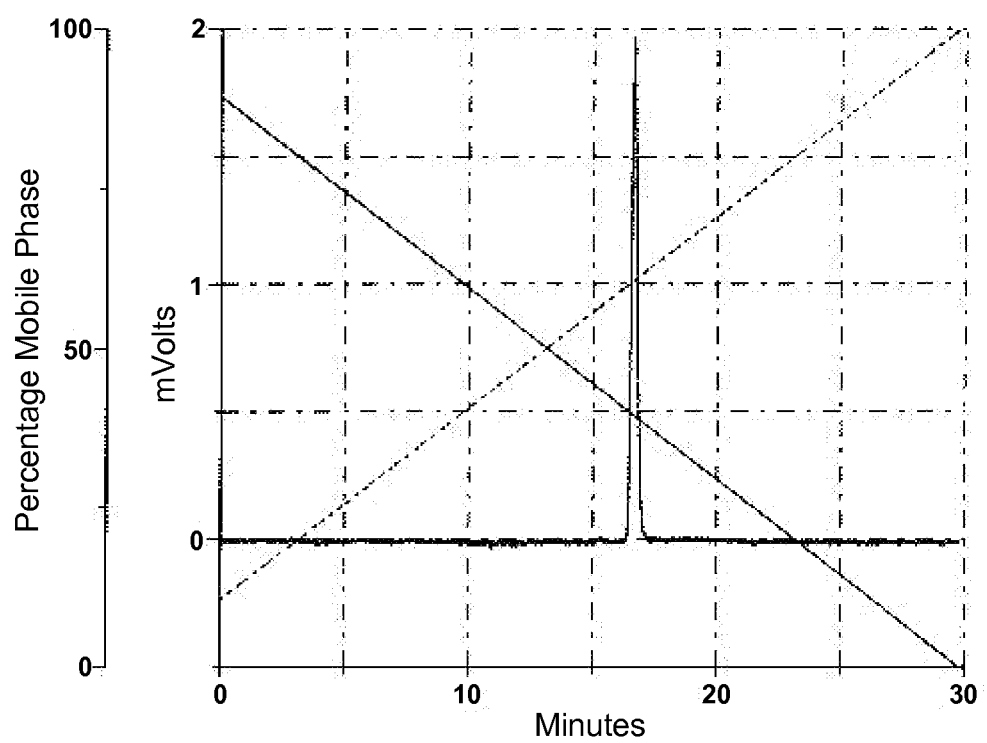
FIG. 4. HPLC trace for poly (ethylene glycol) monomethyl ether-fluorocarbon-DSPE conjugate (1). The diagonal lines show the used acetonitrile/water solvent gradient.

FIG. 4 provides a HPLC trace for poly (ethylene glycol) monomethyl ether-fluorocarbon-DSPE conjugate (1). The diagonal lines show the used acetonitrile/water solvent gradient.

Preparation of Samples for DLS Studies.

Samples were prepared by dissolving 1 in dichloromethane and subsequently concentrating the solution in vacuo to give a thin film. This was reconstituted in water so that the concentration of the solution was 1.25 mg/mL. The solution was then sonicated for 15 minutes and allowed to equilibrate for 30 minutes. The solution was passed through a 0.20 μm filter directly into a quartz cuvette used for the measurements. The data were collected and analyzed in triplicate.

Preparation of Samples for CMC Determination.

The samples for CMC determination were prepared by first transferring a solution of pyrene in acetone (12 μL of a 100 μM solution) to clean, dry 2 dram vials. The acetone was removed in vacuo and solutions of polymer in water were added so that the final pyrene concentration was 0.5 μM. The vials were then heated to 70° C. with good stirring in an oil bath for 1.5 hours, and then allowed to equilibrate at room temperature for 2 hours with no stirring. The solutions were transferred directly to a clean, dry cuvette used for the measurements. Data for each concentration were obtained in triplicate, and the reported values are the average of these measurements.

REFERENCES AND NOTES

1. Torchilin, V. P. CMLS 2004, 61, 2549-2559.
2. Strickley, R. G. Pharm. Res. 2004, 21, 201-230.
3. Torchilin, V. P. J. Controlled Release 2001, 73, 137-172.
4. Lavasanifar, A.; Samuel, J.; Kwon, G. Adv. Drug Delivery Rev. 2002, 54, 169-190.
5. Lukyanov, A. N.; Torchilin, V. P. Adv. Drug Delivery Rev. 2004, 56, 1273-1289.
6. Krafft, M. P. In Handbook of Fluorous Chemistry; Gladysz, J. A., Curran, D. P., Horvath, I. T., Eds.; Wiley-VCH: Weinheim, 2004; Chapter 12.
7. Kissa, E. Fluorinated Surfactants and Repellents, 2nd ed.; Surfactant Science Series; Marcel Dekker New York, 2001; Vol. 97.
8. Riess, J. G. Tetrahedron 2002, 58, 4113-4131.
9. Krafft, M. P. Adv. Drug Delivery Rev. 2001, 47, 209-228.
10. Vierling, P.; Santaella, C.; Greiner, J. J. Fluorine Chem. 2001, 107, 337-354.
11. Hoang, K. C.; Mecozzi, S. Langmuir 2004, 20, 7347-7350.
12. Harris, J. M.; Chess, R. B. Nat. Rev. Drug Discovery 2003, 2, 214-221.
13. Gabizon, A.; Barenholz, Y.; Bialer, M. Pharm. Res. 1993, 10, 703-708.
14. van Etten, E. W. M.; van Vianen, W.; Tijhuis, R.; Storm, G.; Bakker-Woudenberg, I. J. Controlled Release 1995, 37, 123-129.
15. Kwon, G. S.; Kuldipkumar, A.; Tan, Y.; Andes, D. PMSE Preprr. 2003, 89, 50-51.
16. Krishnadas, A.; Rubinstein, I.; Onyuksel, H. Pharm. Res. 2003, 20, 297-302.
17. Ashok, B.; Arleth, L.; Hjelm, R. P.; Rubinstein, I.; Onyuksel, H. J. Pharm. Sci. 2004, 93, 2476-2487.
18. Preparation and characterization of compounds 1-6 are available as Supplementry data.
19. Zalipsky, S. Bioconjugate Chem. 1993, 4, 296-299.
20. The samples for DLS studies were prepared by dissolving 1 in dichloromethane and subsequently concentrating the solution in vacuo to give a thin film. This was reconstituted in water so that the concentration of the solution was 1.25 mg/mL. The solution was then sonicated for 15 min and allowed to equilibrate for 30 min. The solution was passed through a 0.20 mm filter directly into a quartz cuvette used for the measurements. The data were collected and analyzed in triplicate.
21. Kalyanasundaram, K.; Thomas, J. K. J. Am. Chem. Soc. 1977, 99, 2039-2044.

22. Dong, D. C.; Winnik, M. A. Can. J. Chem. 1984, 62, 2560-2565.
23. The samples for CMC determination were prepared by first transferring a solution of pyrene in acetone (12 mL of a 100 mM solution) to clean, dry 2 dram vials. The acetone was removed in vacuo and solutions of polymer in water were added so that the final pyrene concentration was 0.5 mM. The vials were then heated to 70° C. with good stirring in an oil bath for 1.5 h, and then allowed to equilibrate at room temperature for 2 h with no stirring. The solutions were transferred directly to a clean, dry cuvette used for the measurements. Data for each concentration were obtained in triplicate, and the reported values are the average of these measurements.

Methods of this invention may further comprise the step of administering a "therapeutically effective amount" of the present therapeutic formulations, including aqueous-based therapeutic formulations comprising therapeutic agents encapsulated by a supramolecular structures, such as miceles. The term "therapeutically effective amount," as used herein, refers to the amount of the therapeutic formulation, that, when administered to the individual is effective to establish and, optionally maintain or regulate, a desired therapeutic condition in a patient, such as a condition for treatment of a disease condition or pre-disease condition. As is understood in the art, the therapeutically effective amount of a given compound or formulation will depend at least in part upon the mode of administration (e.g. intravenous administration), any carrier or vehicle employed, and the specific individual to whom the formulation is to be administered (age, weight, condition, sex, etc.). The dosage requirements need to achieve the "therapeutically effective amount" vary with the particular formulations employed, the route of administration, and clinical objectives. Based on the results obtained in standard pharmacological test procedures, projected daily dosages of active compound (e.g. fluorinated volatile anesthetic) can be determined as is understood in the art.

Any suitable form of administration can be employed in connection with the therapeutic formulations of the present invention. The therapeutic formulations of this invention can be administered intravenously, in oral dosage forms, intraperitoneally, subcutaneously, or intramuscularly, all using dosage forms well known to those of ordinary skill in the pharmaceutical arts.

The therapeutic formulations of this invention can be administered alone, but may be administered with a pharmaceutical carrier selected upon the basis of the chosen route of administration and standard pharmaceutical practice.

The therapeutic formulations of this invention and medicaments of this invention may further comprise one or more pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

Statements Regarding Incorporation by Reference and Variations

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The following references relate to block copolymer compositions for solubilization, administration and delivery of therapeutic agents, and are hereby incorporated by reference in their entireties; (1) "Development of amphiphilic diblock copolymers as micellar carriers of taxol", Zhang, X, Jackson, J. K, and Burt, H. M., International Journal of Pharmaceutics, 132 (1996), 195-206; (2) "In vitro release of the mTOR inhibitor rapamycin from poly(ethylene glycol)-b-poly(ε-caprolactone) micelles", and Forrest, M. L, Won, C. Y, Malick, A. M., and Kwon, G. S., Journal of Controlled Release, 110 (2006) 370-377;

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed as if separately set forth. This invention is not to be limited by the embodiments disclosed, including any shown in the drawings or exemplified in the specification, which are given by way of example or illustration and not of limitation. The scope of the invention shall be limited only by the claims.

Any suitable form of administration can be employed in connection with the therapeutic compositions and formulations of the present invention. The therapeutic compositions and formulations of this invention can be administered intravenously, in oral dosage forms, intraperitoneally, subcutaneously, or intramuscularly, all using dosage forms well known to those of ordinary skill in the pharmaceutical arts.

The therapeutic compositions and formulations of this invention can be administered alone, but may be administered with a pharmaceutical carrier selected upon the basis of the chosen route of administration and standard pharmaceutical practice.

The therapeutic compositions and formulations of this invention and medicaments of this invention may further comprise one or more pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

This invention additionally relates to the use of semi-fluorinated block copolymers in the manufacture of a medicament for delivery of pharmaceutical compositions. More specifically, the invention relates to the use of semi-fluorinated block copolymers having a hydrophilic block, a fluorophilic block and a hydrophobic group in the manufacture of a medicament for delivery of hydrophobic and fluorophilic therapeutic agents. In specific embodiments the medicament manufactured is in the form of a colloidal suspension for intravenous, topical or oral administration. In specific embodiments, the medicament further comprises a pharmaceutically acceptable carrier or diluent and particularly a carrier or diluent suitable for intravenous administration.

We claim:

1. A therapeutic formulation for delivering a hydrophobic drug or fluorophilic therapeutic agent to a patient, said formulation comprising:
said hydrophobic drug or fluorophilic therapeutic agent; and semi-fluorinated block copolymers, wherein each of said semi-fluorinated block copolymers comprises a hydrophilic block, a fluorophilic block, and a hydrophobic group; wherein said fluorophilic block of each of said semi-fluorinated block copolymers is positioned between said hydrophilic block and said hydrophobic group,
wherein said hydrophobic group is a distearoyl-glycero-phosphoethanolamine;
wherein said hydrophilic block is a poly(ethylene glycol) block having a molecular weight selected over the range of 1000 g mol−1 to 12,000 g mol−1; and
wherein said fluorophilic block is a perfluorinated alkyl chain having a length of 6 to 20 carbons.

2. The therapeutic formulation of claim 1 wherein said perfluorinated alkyl chain has between 12 to 40 carbon-fluorine bonds.

3. The therapeutic formulation of claim 1 wherein said perfluorinated alkyl chain has a length of 8 carbons.

4. The therapeutic formulation of claim 1 wherein said hydrophilic block is a poly(ethylene glycol) block having a molecular weight of 5000 g mol⁻¹.

5. The therapeutic formulation of claim 1 wherein said hydrophobic group is 1,2-distearoyl-S,N-glycero-3-phosphoethanolamine.

6. The therapeutic formulation of claim 1 wherein said semi-fluorinated block copolymers have the chemical formula:

wherein n is selected from the range of 20 to 240, and m is selected from the range of 6 to 20;

wherein $R_1$ is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group;

wherein the [Hydrophobic group] is distearoyl-glycero-phosphoethanolamine;

wherein $L_1$ is a first linking group selected from the group consisting of an alkyl group, alkenyl group, carbonyl group, ester group, amide group, phosphate group, disulfide group and any combination of these, and wherein x equals 0 or 1; and wherein $L_2$ is a second linking group selected from the group consisting of an alkyl group, alkenyl group, carbonyl group, ester group, amide group, phosphate group and any combination of these, and wherein y equals 0 or 1.

7. The therapeutic formulation of claim 6 wherein said semi-fluorinated block copolymers have the chemical formula:

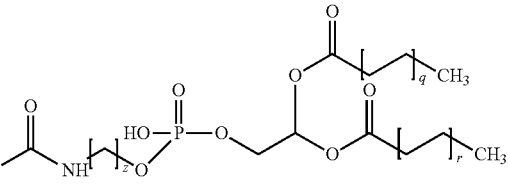

wherein z is selected from the range of 1 to 10, q is 8, and r is 8.

8. The therapeutic formulation of claim 1 wherein said hydrophobic drug is paclitaxel, rapamycin, geldanamycin, doxorubicin, or amophotericin-B.

9. The therapeutic formulation of claim 1 wherein said hydrophobic drug is functionalized via addition of a fluorophilic group.

10. The therapeutic formulation of claim 1 further comprising an aqueous solution.

11. The therapeutic formulation of claim 1 wherein said semi-fluorinated block copolymers self assemble in aqueous solution to form a supramolecular structure that at least partially encapsulates said hydrophobic drug.

12. The therapeutic formulation of claim 11 wherein said supramolecular structure is selected from the group consisting of a micelle, a vesicle, a bilayer, a folded sheet and a tubular micelle.

13. The therapeutic formulation of claim 11 wherein said supramolecular structure has an interior hydrophobic core comprising hydrophobic groups of said semi-fluorinated block copolymers, an intermediate fluorophilic portion comprising fluorophilic blocks of said semi-fluorinated block copolymers and an exterior hydrophilic portion comprising hydrophilic blocks of said semi-fluorinated block copolymers;
wherein said hydrophilic portion is separated from said hydrophobic core by said intermediate fluorophilic portion.

14. The therapeutic formulation of claim 13 wherein said hydrophobic drug encapsulated by said supramolecular structure is provided in said hydrophobic core, in said intermediate fluorophilic portion or in both said hydrophobic core and intermediate fluorophilic portion supramolecular structure.

15. The therapeutic formulation of claim 1 wherein said semi-fluorinated block copolymers have a critical micelle concentration less than or equal to 1 µM.

16. The therapeutic formulation of claim 11 wherein said supramolecular structure has a cross sectional physical dimension selected over the range of about 10 nanometers to about to about 100 nanometers.

17. A method of administering a hydrophobic drug or fluorophilic therapeutic agent to a patient in need of treatment; said method comprising the steps of: providing a therapeutic formulation comprising said hydrophobic drug or fluorophilic therapeutic agent,
and semi-fluorinated block copolymers in an aqueous solution, wherein each of said semi-fluorinated block copolymers comprise a hydrophilic block, a fluorophilic block, and a hydrophobic group; wherein said fluorophilic block of each of said semi-fluorinated block copolymers is positioned between said hydrophilic block and said hydrophobic group,
wherein said hydrophobic group is 1,2-distearoyl-S,N-glycero-3-phosphoethanolamine;
wherein said hydrophilic block is a poly(ethylene glycol) block having a molecular weight selected over the range of 1000 g mol−1 to 12,000 g mol−1; and
wherein said fluorophilic block is a perfluorinated alkyl chain having a length of 6 to 20 carbons; and
delivering said therapeutic formulation to said patient.

18. A method of solubilizing a hydrophobic drug or fluorophilic therapeutic agent, said method comprising the steps of:

providing said hydrophobic drug or fluorophilic therapeutic agent,
and semi-fluorinated block copolymers in an aqueous solution, wherein each of said semi-fluorinated block copolymers comprises a hydrophilic block, a fluorophilic block, and a hydrophobic group; wherein said fluorophilic block of each of said semi-fluorinated block copolymers is positioned between said hydrophilic block and said hydrophobic group,
wherein said hydrophobic group is 1,2-distearoyl-S,N-glycero-3-phosphoethanolamine;
wherein said hydrophilic block is a poly(ethylene glycol) block having a molecular weight selected over the range of 1000 g mol−1 to 12,000 g mol−1; and
wherein said fluorophilic block is a perfluorinated alkyl chain having a length of 6 to 20 carbons; and wherein said semi-fluorinated block copolymers self assemble in said aqueous solution to form a supramolecular structure that at least partially encapsulates said hydrophobic drug or fluorophilic therapeutic agent, thereby solubilizing said hydrophobic drug or fluorophilic therapeutic agent.

19. A method of decreasing the toxicity of a hydrophobic drug or fluorophilic therapeutic agent, said method comprising the steps of:

providing said hydrophobic drug or fluorophilic therapeutic agent, and semi-fluorinated block copolymers in an aqueous solution, wherein each of said semi-fluorinated block copolymers comprises a hydrophilic block, a fluorophilic block, and a hydrophobic group; wherein said fluorophilic block of each of said semi-fluorinated block copolymers is positioned between said hydrophilic block and said hydrophobic group,
wherein said hydrophobic group is 1,2-distearoyl-S,N-glycero-3-phosphoethanolamine;
wherein said hydrophilic block is a poly(ethylene glycol) block having a molecular weight selected over the range of 1000 g mol−1 to 12,000 g mol−1; and
wherein said fluorophilic block is a perfluorinated alkyl chain having a length of 6 to 20 carbons; and wherein said semi-fluorinated block copolymers self assemble in said aqueous solution to form a supramolecular structure that at least partially encapsulates said hydrophobic drug or fluorophilic therapeutic agent, thereby decreasing the toxicity of said hydrophobic drug or fluorophilic therapeutic agent.

20. A semi-fluorinated block copolymer having the chemical formula:

$$R_1\text{-}[\text{CH}_2\text{CH}_2\text{O}]_n\text{-}[L_1]_x\text{-}[CF_2]_m\text{-}[L_2]_y\text{-}[\text{Hydrophobic Group}]$$

wherein n is selected from the range of 20 to 240, and m is selected from the range of 6 to 20;
wherein R1 is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group;
wherein the [Hydrophobic group] is 1,2-distearoyl-S,N-glycero-3-phosphoethanolamine;
wherein L1 is a first linking group selected from the group consisting of an alkyl group, alkenyl group, carbonyl group, ester group, amide group, phosphate group, disulfide group and any combination of these, and wherein x equals 0 or 1; and
wherein L2 is a second linking group selected from the group consisting of an alkyl group, alkenyl group, carbonyl group, ester group, amide group, phosphate group and any combination of these, and wherein y equals 0 or 1.

21. The semi-fluorinated block copolymer of claim 20 having the chemical formula:

$$R_1\text{-}[\text{CH}_2\text{CH}_2\text{O}]_n\text{-}[CF_2]_m\text{-}O\text{-}C(=O)\text{-}NH\text{-}[CH_2]_z\text{-}O\text{-}P(=O)(OH)\text{-}O\text{-}CH_2\text{-}CH(O\text{-}C(=O)\text{-}[CH_2]_r\text{-}CH_3)\text{-}CH_2\text{-}O\text{-}C(=O)\text{-}[CH_2]_q\text{-}CH_3$$

wherein z is selected from the range of 1 to 10, q is 8, and r is 8.

22. The therapeutic formulation of claim 1 wherein said hydrophobic drug is Paclitaxel.

23. The therapeutic formulation of claim 1 wherein said hydrophobic drug is Rapamycin.

24. The therapeutic formulation of claim 1 wherein said hydrophobic drug is 17-AAG.

25. The therapeutic formulation of claim 1 wherein said hydrophobic drug is Amphotericin B.

* * * * *